United States Patent [19]
Sahagen

[11] Patent Number: 5,526,112
[45] Date of Patent: Jun. 11, 1996

[54] PROBE FOR MONITORING A FLUID MEDIUM

[76] Inventor: Armen N. Sahagen, 16757 Bolero La., Huntington Beach, Calif. 92649

[21] Appl. No.: 27,189

[22] Filed: Mar. 5, 1993

[51] Int. Cl.⁶ ............................. G01N 21/00; A61B 5/00; G01L 7/08
[52] U.S. Cl. ............... 356/72; 356/336; 356/436; 250/227.11; 250/574; 128/667; 73/715; 73/720
[58] Field of Search ............... 356/72, 128, 441, 356/336, 436; 250/231.11, 227.11, 574; 128/667; 73/705, 714, 715, 722

[56] References Cited

U.S. PATENT DOCUMENTS

| | | | |
|---|---|---|---|
| 3,654,579 | 4/1972 | Kurtz et al. | 338/2 |
| 4,085,620 | 4/1978 | Tanaka | 73/727 |
| 4,127,840 | 11/1978 | House | 338/4 |
| 4,166,384 | 9/1979 | Matsuda et al. | 73/141 A |
| 4,444,516 | 4/1984 | Dostoomian et al. | 374/131 |
| 4,487,206 | 12/1984 | Aagard | 128/667 |
| 4,569,570 | 2/1986 | Brogårdh et al. | 350/96.34 |
| 4,589,286 | 5/1986 | Berthold, III | 73/715 |
| 4,600,912 | 7/1986 | Marks et al. | 338/42 |
| 4,611,600 | 9/1986 | Cohen | 128/667 |
| 4,670,649 | 6/1987 | Senior et al. | 73/705 |
| 4,689,483 | 8/1987 | Weinberger | 250/231 R |
| 4,691,575 | 9/1987 | Sonderegger et al. | 73/756 |
| 4,771,638 | 9/1988 | Sugiyama et al. | 73/721 |
| 4,787,396 | 11/1988 | Pidorenko | 128/667 |
| 4,803,992 | 2/1989 | Lemelson | 128/634 |
| 4,824,206 | 4/1989 | Klainer et al. | 350/96.29 |
| 4,893,935 | 1/1990 | Mandel et al. | 356/436 |
| 4,909,588 | 3/1990 | Harner et al. | 350/96.20 |
| 4,970,903 | 11/1990 | Hanson | 73/862.59 |
| 4,994,680 | 2/1991 | Brügmanal | 250/227.11 |
| 4,994,781 | 2/1991 | Sahagen | 338/47 |
| 5,088,329 | 2/1992 | Sahagen | 73/727 |
| 5,107,847 | 4/1992 | Knote et al. | 73/705 |
| 5,146,083 | 9/1992 | Zuckerwar et al. | 250/227.21 |
| 5,206,711 | 4/1993 | Berthold et al. | 356/436 |
| 5,241,368 | 8/1993 | Ponstingi et al. | 356/73 |
| 5,280,788 | 1/1994 | Janes et al. | 128/665 |
| 5,291,030 | 3/1994 | Brors | 356/436 |
| 5,313,957 | 5/1994 | Little | 128/748 |

FOREIGN PATENT DOCUMENTS

| | | |
|---|---|---|
| 0189492A1 | 8/1986 | European Pat. Off. . |
| 0336437A2 | 10/1989 | European Pat. Off. . |
| 1548380 | 10/1968 | France . |
| 2940955A1 | 4/1981 | Germany . |

OTHER PUBLICATIONS

Pierre Desgoutte et al., *Les capteurs en instrumentation industrielle* (no translation provided).
Cross, *Practical Infra-Red Spectroscopy* at 36 (1964) [copy not readily available].

*Primary Examiner*—Rolf Hille
*Assistant Examiner*—David Hardy
*Attorney, Agent, or Firm*—Stetina Brunda & Buyan

[57] ABSTRACT

A probe for monitoring a fluid medium employing at least one fiber optic emitting a wave into the fluid medium. The fluid medium scatters or causes luminescence of the emitted wave which is then collected by at least one fiber optic. The probe includes a base having a hole and a window covering the hole of the base, wherein the window transmits electromagnetic waves. The probe collects scattered and luminescence of waves through one or more fiber optics placed behind the window and transmits the waves to a spectrometer connected to a computer which can analyze the fluid medium on a real-time on-line basis. Piezoresistive and temperature sensing elements are deposited on the window which can also serve as a force collector diaphragm. The elements are located primarily on the periphery of the diaphragm leaving a part of the diaphragm open for transmission and collection of the waves.

84 Claims, 11 Drawing Sheets

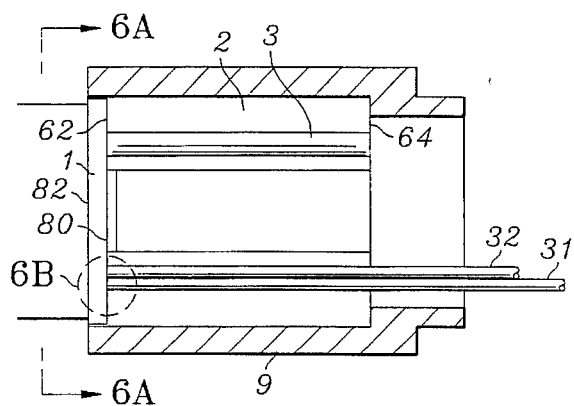
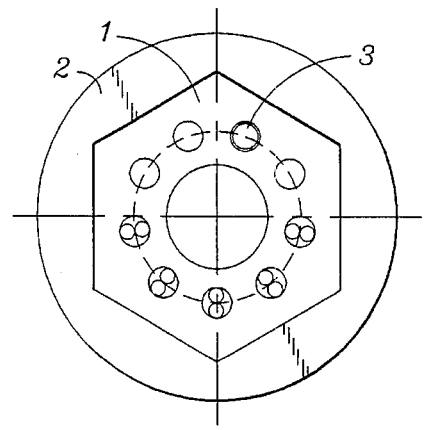
FIG. 6  FIG. 6A
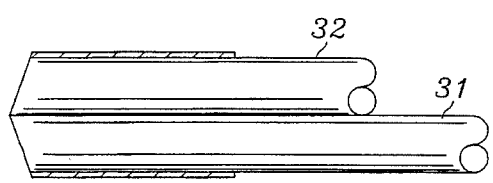
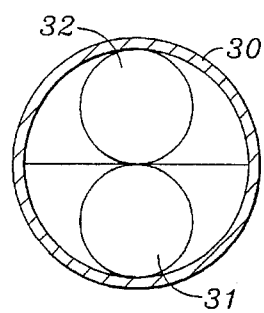
FIG. 6B  FIG. 6C
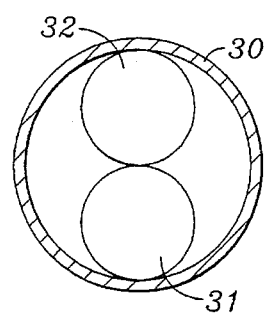
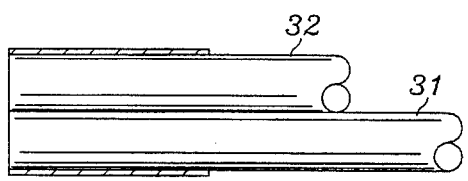
FIG. 6D  FIG. 6E

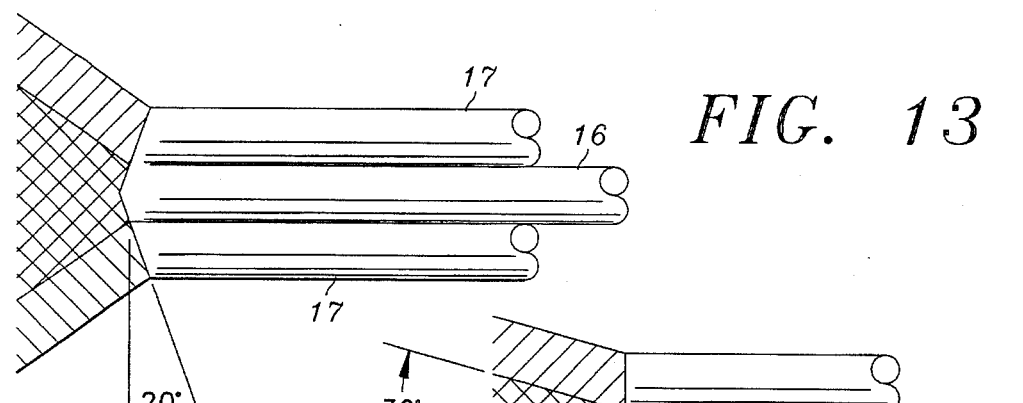
FIG. 13
FIG. 14A
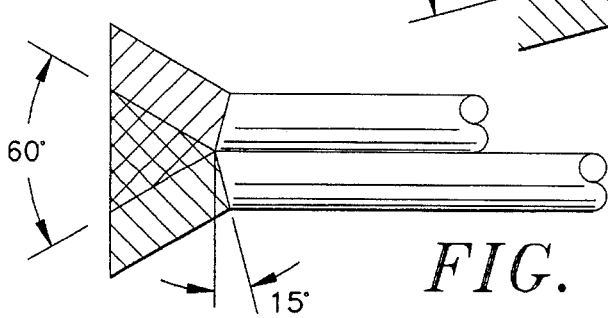
FIG. 14B
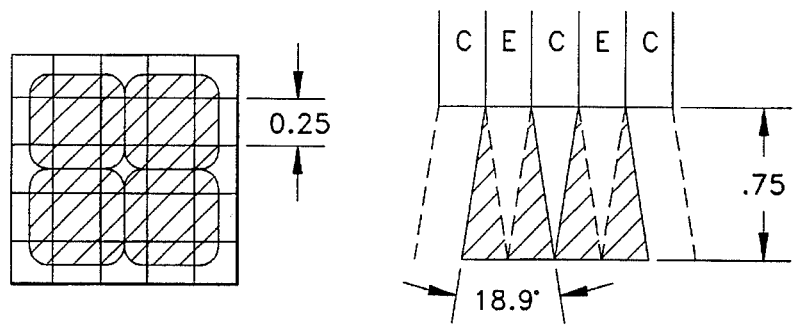
FIG. 15A
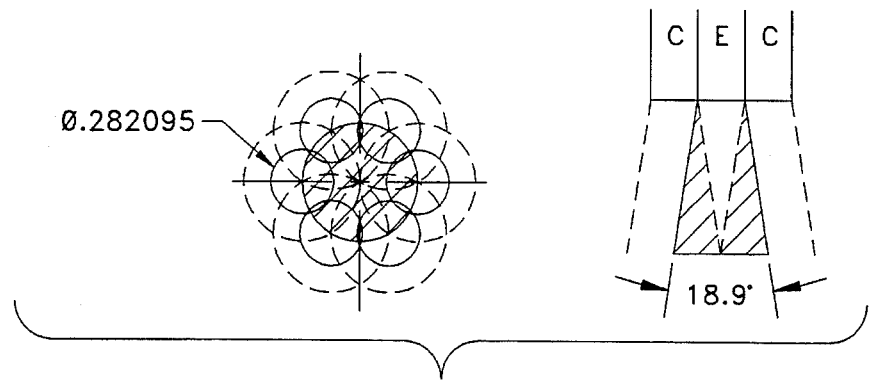
FIG. 15B

PROBE FOR MONITORING A FLUID MEDIUM

BACKGROUND OF THE INVENTION

1. Field of the Invention

The present invention relates to a probe for monitoring a fluid medium. More specifically, the invention relates to a probe including at least one fiber optic for emitting wave(s) into the fluid medium which scatters or causes luminescence of the emitted wave(s) which are then collected by at least one fiber optic.

2. Description of the Related Art

When an electromagnetic wave penetrates a fluid medium it may collide with one or more atoms. Some of the energy remaining after the collision will be transformed into scattering wave(s). In turn the scattering waves may produce other scattered waves. Various attempts have been made to collect such scattered waves after interaction with a fluid medium to monitor and analyze the fluid medium. In general, monitoring the fluid medium may include performing quantitative and qualitative analysis of elements, compounds and/or mixtures making up the fluid medium.

In addition, when an incident electromagnetic wave penetrates a fluid medium it may collide with one or more atom producing visible light a phenomena is referred to as luminescence. For example, when an electromagnetic wave collides with a phosphorous atom it may luminescence in the visible light range. Again the amount and type of luminescence reveals certain characteristics about the fluid medium.

The current state of probes has greatly limited the usefulness of Raman spectrometers to analyze fluid medium based on luminescence or scattered electromagnetic waves. One of the biggest limitations is low generation and collection efficiency of existing probes. For example, if a Raman spectrometer is to be used to analyze sparse Rayleigh photons, the probe must have larger acceptance angles or higher grazing fields than apparently are available.

FIG. 1 illustrates the limitations of a conventional fiber optic pair. To understand the problem consider that fiber optic 4 and 5 respectively emit and collect waves in cone-shape acceptance cones 31 and 32. Each acceptance cone 31 and 32 is bound by a divergent angle referred to as the numerical aperture which is defined by factors such as the type and size of the fiber optic core and cladding. A portion of the acceptance cones 31 and 32 will overlap at a volume 33 indicated by cross-hatching. Because the collecting fiber optic 5 can only collect that portion of the emitted waves in volume 33, the fiber optic pair of FIG. 1 will only collect reflected, scattered or Rayleigh waves within the limits of volume 33. This volume 33 is referred to as the "grazing field" and the larger the grazing field the higher the collection efficiency.

A conventional fiber optic typically has a numerical aperture of 10°. Therefore, its grazing field will be quite limited and its collection efficiency low. Thus, conventional fiber optic pairs greatly limit the Raman spectrometers. Yet certain applications for this type of analysis exist in industry for real-time on-line monitoring of a fluid medium.

For example, in the polymer industry to monitor the temperature and pressure and composition of a polymer melt would be highly desirable. In other industries, involving chemical processing plants, oil refinery and distillation plants and smog and pollution detection, on-line monitoring of the pressure, temperature and composition of the fluid mediums is essential. However, apparently no existing probe can do such monitoring under these conditions. At best, the industry employs piezoresistive pressure transducers to monitor the high pressure and temperatures of polymer melts such as those described in U.S. Pat. Nos. 4,994,781 and 5,088,329 to Sahagen.

Such piezoresistive pressure transducers employ a pressure force collector diaphragm having one or more piezoresistive elements mounted thereon. The diaphragm with the piezoresistive elements is typically placed in a pressure cell base which maintains a low pressure or vacuum on one side of the diaphragm. External fluid medium under pressure contacts the other side of the diaphragm. A voltage is placed across the piezoresistive element(s) and as the diaphragm flexes in response to a pressure changes, a resistance change in the piezoresistive element(s) results in a change in the current flowing through the piezoresistive element(s).

Apparently, however, there is no on-line monitoring of the composition of polymers or other fluid medium at high temperatures and pressures. Thus, the composition of the polymer melts are not known on a real-time basis at high temperatures and pressures. The pressure and temperature of such polymer melts can reach up to 15,000 psi and to 800° F. and above. In fact, in some polymer melt processes the pressure may go up to 1500° F. or higher and the pressures up to 50,000 psi. Furthermore, in certain applications, the polymer melt will be a slurry viscous fluid having corrosive and abrasive properties which readily abrade and degrade conventional steel alloys and stainless steel posing additional obstacles to monitoring the polymer.

As a result, in the polymer industry, the polymer melt process is controlled by off-line sampling. The composition of the polymer melt is typically analyzed on a regular basis by extracting a sample of the polymer melt from the process for laboratory analysis. After analysis, a decision is made whether the polymer melt is suitable for production. Because such a laboratory analysis can require as much as four hours to perform off-line sampling can result in the production of considerable material not useful for its intended purpose. A large-scale polymer melt processing plant can generate in excess of $100,000 worth of polymer per hour. Thus, effective on-line monitoring of a high temperature and pressure polymer melt can result in large cost savings by preventing the waste of a large amount of material from which the polymer is derived on a monthly basis in one plant alone. Thus, a probe performing real-time on-line monitoring of not only the pressure and temperature, but also the composition of the polymer melt would be highly desirable. Accordingly, there is a great need in the polymer industry for a durable reliable probe which can monitor the high pressure, high temperature, composition and other physical properties of polymer melts.

In addition, there is a great need in the medical world for monitoring of blood, cancer, and abnormal cell growth within the body without the need for major surgery. For example, sometime surgery must be performed to determine the status or growth of cancer. When cancer is bombarded by certain electromagnetic waves, it will radiate scattered waves or luminescence waves which can be collected and analyzed. The characteristics of such waves will indicate the concentration, growth rate, and other important properties of the cancer. It would be highly desirable to have a probe which can use this phenomena to monitor cancer.

One technique for treatment of cancer in an internal organ involves irradiating the patient's body. Eradicating such cancerous growth can require irradiating both the affected organ and the surrounding tissue with high dosages of radiation. This is because the radiation must penetrate surrounding tissue, bodily fluids and perhaps other organs. This can have an adverse effect on the patient receiving the dosage, which in turn drastically limits the amount and corresponding effectiveness of the dosage.

SUMMARY OF THE INVENTION

The present invention relates to a probe for monitoring a fluid medium. More specifically, the invention relates to a probe for monitoring a fluid medium. The probe includes at least one fiber optic emitting waves into the fluid. The fluid scatters or causes luminescence of the emitted wave which is then collected by at least one fiber optic.

The present invention provides a probe suitable for use in determining the pressure, temperature and composition simultaneously or individually of corrosive and abrasive materials or other fluid mediums in a wide variety of other extreme environments.

The present invention further provides a probe for monitoring a fluid medium, including a base having a hole, a window covering the hole of the base, wherein the window is capable of transmitting electromagnetic waves into the fluid and the collection efficiency of the probe is adequate to analyze scattered or luminescence.

The present invention further provides multifiber optic collectors wherein at least one end of a collecting fiber optic has an angle from 5° to 45° with respect to the major surface of a window. Such an embodiment, along with other modifications to the collecting fiber optic end offers a large grazing field. The embodiment therefore renders it possible and efficient to collect all types of scattered waves including sparse Rayleigh waves.

In another embodiment, the present invention provides means to transmit electromagnetic waves into a fluid medium and collect the waves scattered or dispersed from the fluid medium. Such fluid medium may be extremely corrosive, abrasive, at high temperatures and high pressures, either simultaneously or separately.

In another embodiment, the present invention provides means for emitting electromagnetic waves into the fluid medium, where the electromagnetic waves bounce back after penetration into the fluid medium through dispersion in a fluid medium. In another embodiment, the present invention collects dispersed electromagnetic waves through a fiber optic placed behind a window to a fluid medium and transmits the waves to a spectrometer operably connected to a computer which analyzes the fluid composition on a real-time on-line basis.

In another embodiment, the present invention provides means for analyzing the composition and monitoring the pressure and temperature of the fluid medium either simultaneously or individually. Pressure and temperature sensing elements are disposed on areas of a force collector diaphragm. The elements are preferably located so as to leave part of the diaphragm open for the transmission and collection of electromagnetic waves.

In another embodiment, the present invention provides a window transparent to certain electromagnetic waves therefore allowing certain wavelength bands such as in the infrared spectrum, near-infrared, medium infrared, to be filtered by the window.

In another embodiment, the present invention provides a probe having means for electromagnetic waves to be transmitted into the fluid medium and scattered by the fluid medium to the means. The electromagnetic waves are collected through a fiber optic placed behind the means. Such means make the probe suitable for use with fluid mediums which are extremely corrosive, abrasive, and at high temperatures and high pressures.

The present invention further provides a force collector diaphragm which acts as a window to isolate the high pressure, high temperature fluid medium from the outside world and as a lens to collect scattered waves more efficiently.

The present invention further provides means wherein fiber optics are kept under compression against the window therefore compensating for any difference in the thermal expansion or contraction of the fiber optic and overall assembly due to temperature variation.

This invention relates to means for increasing the grazing field or collection cone in order to provide photon collection efficiency large enough to make possible the use of certain principles such as those used in Raman Spectroscopic Analyzers.

The present invention provides means for transmitting a concentrated dosage of electromagnetic radiation to a local region in a manner which renders the radiation effective and promotes local disintegration, eradication and treatment of cancerous growth. The present invention further provides means for simultaneously applying the radiation and monitoring the results such that it is possible to administer larger doses of radiation at more frequent intervals.

The present invention provides a combination probe capable of monitoring and eradicating cells in the human body by providing means for monitoring radiation on a real-time on-line basis by collecting luminescence, reflected or scattered waves after interaction and irradiation of the cells.

The present invention further provides an improved fiber optic capable of transmitting and collecting electromagnetic waves of a broader wavelength range than provided by conventional fiber optics.

BRIEF DESCRIPTION OF THE DRAWINGS

The foregoing objects, features and advantages of the invention will become more apparent from the following detailed description of the preferred embodiments taken in conjunction with the accompanying drawings, in which:

FIG. 6 illustrates a electromagnetic window embodiment of the probe permitting individual or simultaneous analysis of specific elements, compounds and/or mixtures.

FIG. 6A is an end view of the probe taken from the fluid medium side along line A—A of FIG. 6.

FIG. 6B is a close up view of cone shaped fiber optic ends taken at section B of FIG. 6.

FIG. 6C is a close up end view of an embodiment of the fiber optic pair taken at section B of FIG. 6.

FIG. 6D is a close up end view of an alternative embodiment of fiber optic pair taken at section B of FIG. 6.

FIG. 6E is close up view of an alternative embodiment of a fiber optic pair and a temperature sensitive element taken from the fluid medium side at section B of FIG. 6.

FIG. 13 illustrates an embodiment of a multifiber optic having a core shaped end.

FIGS. 14A illustrates a conventional fiber optic pair having a grazing field of 30°.

FIGS. 14B illustrates a fiber optic pair having an increased grazing field of 60°.

FIGS. 15A illustrates the grazing field of square fiber optics.

FIG. 15B illustrates the grazing field of round fiber optics.

DETAILED DESCRIPTION OF THE PREFERRED EMBODIMENTS

The following description is the best contemplated mode of carrying out the invention. The description is made for the purpose of illustrating the general principles of the invention and should not be taken in a limiting sense. The scope of the invention is best determined by reference to the appended claim. In the accompanying drawings, like numerals designate like parts.

Figure 2:
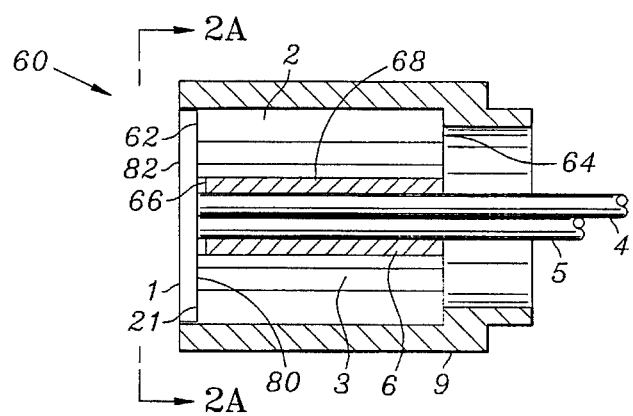
FIG. 2 is a cross-section through an embodiment of the probe of the present invention.

FIG. 2 is a cross-section through a preferred embodiment of the probe 60 of the present invention. The probe 60 includes a window 1 capable of transmitting electromagnetic waves. When the probe 60 has a pressure monitoring function, the window 1 also functions as a force collector diaphragm as described in U.S. Pat. Nos. 4,994,781 and 5,088,329 to Sahagen. These patents are hereby incorporated by reference. For brevity the window 1 will be referred to as a force collector diaphragm 1. The diaphragm 1 can be made of crystalline or amorphous refractory, semiconductor material, intermetallics or metal.

Figure 2A:
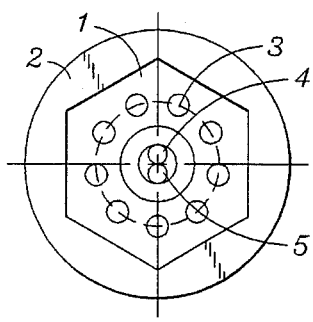
FIG. 2A is an end view of the probe taken from the fluid medium side along line A—A of FIG. 2.

FIG. 2A is an end view of the probe taken from the fluid medium side along line A—A of FIG. 2. As shown in FIG. 2A, the diaphragm 1 is hexagonal, but may be circular, square, triangular or any other shape lending itself to ease of manufacture. The diaphragm 1 can be a thin deflectable diaphragm of single or polycrystalline sapphire having a thickness of 0.003 to 0.070 inches. For example, single crystalline sapphire slices of 0.320 inch diameter and having a thickness of 0.013 to 0.050 inches may be used. The sapphire is preferably grown through the Czochralski process with a 1011 orientation along the C axis. A conventional process can be used to grow the epitaxial single crystal piezoresistive layers on the diaphragm 1.

Some other materials for diaphragm 1 are diamond, quartz, ceramic compounds such as $Al_2O_3$, better known as alumina; BeO beryllium oxide, better known as brylia; silicon nitride; silicon carbide compounds; BeO and $Al_2O_3$, brylia and alumina, better known as chrysoberyl; MgO and $Al_2O_3$, compounds, better known as spinel; zirconium oxide and aluminum oxide systems, better known as zirconia alumina; $SiO_2$ and aluminum compounds, better known as andalusite or silliminite; silicon nitrate and aluminum oxide compounds; and any other metal oxide compound or compound suitable for ceramic processing having a temperature coefficient of expansion of about $1\times10^{-7}/°$ F. to $1\times10^{-3}/°$ F. and a high electrical insulation properties and an optimized thermal conductivity of from 0.020 to 0.700 cal/cm²/cm/sec/° C.

As shown in FIG. 2, the diaphragm 1 is bonded by bonding layer 21 to a pressure cell base 2 of amorphous or crystalline metal oxides, semiconductor materials, metal, metal alloys or a combination thereof. The temperature coefficient of expansion of the base 2 should closely match that of the bonding layer 21 and the diaphragm 1 to permit operation at high temperatures of up to 1500° F. and above and high pressures of up to 50,000 psi and above. The base 2 preferably isolates electrical connectors (not shown) which are threaded through holes 3.

Alumina is a suitable material for the base 2. However, the base 2 can be another material having the following properties: improved heat conductivity to minimize temperature response time, high dielectric constant; non-porous; good adhesion properties for glass ceramic and brazing sealing; and corrosion and abrasion endurance against corrosive environments and abrasive compounds which might be encountered in polymer, plastic, food and other industries.

Some of the other compounds for the base 2 are diamond, quartz and ceramics such as BeO, beryllium oxide, better known as brylia; silicon nitride; silicon carbide compounds; BeO and $Al_2O_3$, brylia and alumina, better known as chrysoberyl; MgO and $Al_2O_3$, compounds, better known as spinel; zirconium oxide and aluminum oxide systems, better known as zirconia alumina; $SiO_2$ and aluminum compounds, better known as andalusite or silliminite; silicon nitrate and aluminum oxide compounds; and any other metal oxide compound or compound suitable for ceramics processing having a temperature coefficient of expansion of $1\times10^{-7}/°$ F. to $1\times10^{-3}/°$ F. and having high electrical insulation properties and an optimized thermal conductivity of from 0.020 to 0.700 cal/cm²/cm/sec/° C. Favorable results can be achieved when the temperature coefficient of expansion of the diaphragm 1 and base 2 substantially match.

The bonding layer 21 is preferably of a ceramic glass with a working temperature of 1500° F. or higher. The bonding layer 21 preferably has a temperature coefficient of expansion of $1\times10^{-7}/°$ F. to $1\times10^{-3}/°$ F. The ceramic glass also known as devitrifying glass can be used for the bonding layer 21. Vitrifying or non-vitrifying ceramic glass or glass, and preferably vitrifying ceramic glass can be applied to the diaphragm 1 and base 2 on proper areas through a conventional technique such as silk screening or doctor blading. Some of the ceramic glass compounds are commercially available from Corning Glass and other sources. One such example is Corning Glass No. 7578.

After applying the ceramic glass to diaphragm 1 and base 2 and performance of a drying cycle, the ceramic glass will bond to and seal the diaphragm 1 and base 2 at temperatures between typically 350° C. to 900° C. depending on the type of ceramic glass selected. At this temperature range, the ceramic glass goes through a nucleation and a transformation stage and becomes a solid substance that, unlike glass, will not become plastic as temperature increases and will not melt at temperatures of up to 1200° C. Through selection of appropriate materials matching temperature coefficients of expansion can be obtained so the bonding layer 21 closely matches that of diaphragm 1 and base 2. Matching the temperature coefficients of expansion is important to reduce or eliminate microscopic cracks from arising from repeated heating and cooling cycles occurring during operation.

As shown in FIG. 2A, the base 2 is cylindrical. However, it could be hexagonal, square, triangular or any other shape lending itself to ease of manufacture. As shown in FIG. 2, the base 2 has an upper surface 62 with a cavity 66, a lower surface 64 and a hole 68 extending from the upper surface 62 to the lower surface 64.

Fiber optics 4 and 5 reside in a liner 6 which in turn resides in hole 68. The liner 6 is preferably of KOVAR. Polyamide or another suitable high temperature material able to withstand the operating temperature fixes the fiber optics 4 and 5 and liner 6 together. This facilitates the handling, housing, forming and polishing of the ends of the otherwise fragile fiber optics 4 and 5. Fiber optics 4 and 5 may slide in hole 68 to compensate for temperature expansion and contraction.

The diaphragm 1, the base 2 and the fiber optics 4 and 5 are housed in an external sleeve 9. The sleeve 9 is preferably made of KOVAR and fastens to the outside of the base 2. Silver copper brazing, for example, is used to fasten the sleeve 9 to the base 2. The sleeve 9 serves to strengthen the base 2 and provides hermeticity. Additional housings and assemblies can be attached to sleeve 9. The sleeve 9 extends flush with the base 2 and also serves to protect the diaphragm 1.

In an illustrative embodiment, a source (not shown) provides electromagnetic waves to an end of the fiber optic 4. The waves are transmitted through the fiber optic 4 and emitted from the opposite end of the fiber optic 4 then through the diaphragm 1 and then into the fluid medium to produce luminescence or scattered waves. Some of these waves are collected by fiber optic 5 and are transmitted to the external world for analysis by a spectrometer or other analytical test equipment.

Figure 4:
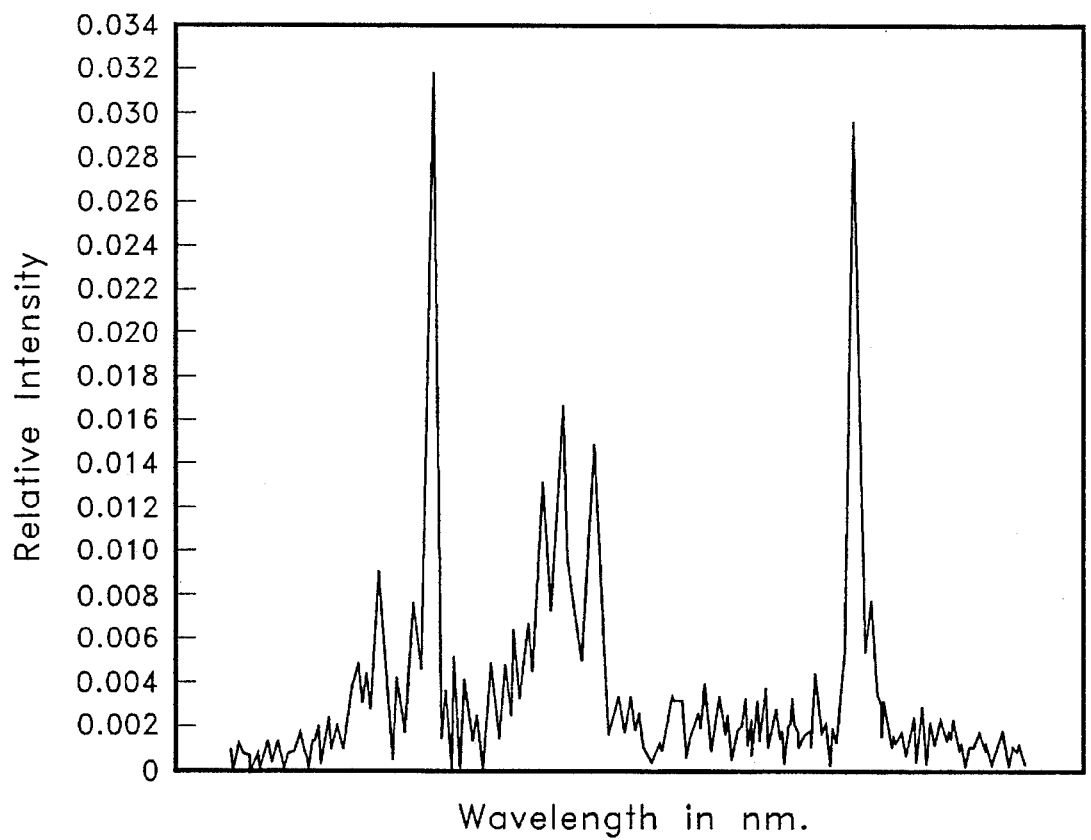
FIG. 4 is a scattering curve.

A fluid medium (e.g. gas or liquid) differentially scatters over an electromagnetic wavelength range. As shown in FIG. 4, a spectrometer can generate a scattering curve with peaks and valleys based on the collected waves discussed earlier. This is useful because any element, mixture, or compound generates a unique scattering curve having peaks and valleys at certain characteristic wavelengths. The location of and the magnitude of the peaks will indicate the type of and concentration of the elements, compounds or mixtures.

FIG. 2A is a sectional end view of probe 60 taken along section A—A of FIG. 2. FIG. 2A shows the relative location of the fiber optics 4 and 5, the diaphragm 1 and the base 2. The holes 3 provide access to piezoresistive and temperature sensitive elements described below.

Fiber optics 4 and 5 need to transmit substantially all of the waves to avoid inaccurate detection. An embodiment for analyzing the electromagnetic waves in the near-infrared to medium-infrared range, and more particularly from 0.9 microns to 4 microns, an embodiment provides that the fiber optics 4 and 5 be from 200 angstrom to 1000 angstroms in diameter and be constructed of sapphire or another suitable material.

Figure 3:
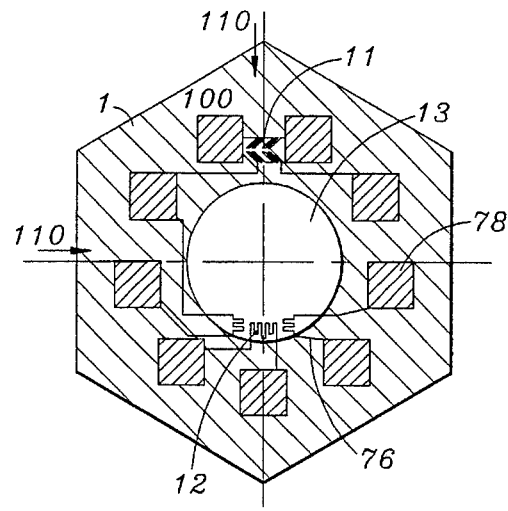
FIG. 3 illustrates an embodiment of the diaphragm and an arrangement of the contact pads, the connecting arms, the piezoresistive elements in a Wheatstone bridge and the temperature sensing elements on the diaphragm.

FIG. 3 shows an end view of a probe 60. Probe 60 includes a force collecting diaphragm 1, an electromagnetically transparent window 13, piezoresistive elements 12 and the temperature sensitive elements 11. Piezoresistive elements 12 and temperature sensitive elements 11 are deposited on the diaphragm 1 through epitaxial deposition, chemical vapor deposition, sputtering or some other conventional technique.

The temperature sensitive elements 11 and the piezoresistive elements 12 are preferably epitaxially grown or otherwise deposited on single crystal or polycrystalline sapphire diaphragms. The piezoresistive elements 12 are grown on an unsupported part near the edge of cavity 66 of the first major surface 80 (FIG. 2) of diaphragm 1 facing toward a cavity 66 (FIG. 2) to form a single integral crystal structure with the sapphire diaphragm 1.

Alternatively, the piezoresistive elements 12 can be located anywhere on the unsupported part of diaphragm 1. The piezoresistive elements 12 are from 500 angstroms to 60,000 angstroms in thickness with a preferred thickness range of from 500 to 7,000 angstroms. One preferred piezoresistive material is silicon having an impurity doping of boron in the range of from $5\times10^{17}$ atoms/cm$^3$ to $2\times10^{21}$ atoms/cm$^3$. In another embodiment, silicon from 8000 to 10,000 angstroms in thickness can be deposited on the diaphragm 1 and doped with a P-type dopant such as boron atoms of from about $1\times10^{17}$ to about $5\times10^{21}$ atom/c$^3$ concentration. Additionally, when silicon is used as the piezoresistive pressure sensitive element, the silicon can be doped with boron atoms in the range of from $9\times10^{17}$ to $5\times10^{21}$ atoms/cm$^3$ and preferably from $3\times10^{18}$ to $2\times10^{19}$ atoms/cm$^3$.

The doping is accomplished with standard semiconductor diffusion or ion implantation techniques. Diffusion temperatures in the range of from 1000° C. to 1200° C. can be used when the specified boron concentration is targeted. This provides piezoresistive elements of desirable small temperature coefficient of resistance and a relatively large gauge factor.

Other piezoresistive materials include various silicites, nichrome and various cermet materials. The deposited piezoresistive elements are arranged (using standard photolithographic masking and etching techniques) in a Wheatstone bridge with thin conductive traces connecting the piezoresistive elements to contact pads on the sapphire diaphragm.

Other alloys or elements which have demonstrated applicability as piezoresistive elements, although they lack the high gauge factor of silicon, but have controllable temperature coefficients of resistance are as follows:
1. Pure platinum;
2. Approximately 8% tungsten/balance platinum compounds or other percentages of tungsten;
3. Silicon/platinum compounds, better known as platinum silicites;
4. Nickel/chromium alloys of 20 to 80% chromium and other ratios;
5. Nickel/copper alloys, better known as constantan alloys;
6. Silicon carbide doped with oxygen;
7. Tantalum/aluminum oxide cermets;
8. Aluminum/aluminum oxide cermets;
9. Gold/aluminum oxide cermets;
10. Platinum/aluminum oxide cermets; and
11. Other combinations of the above materials or other materials demonstrating piezoresistive properties on crystalline or amorphous metal oxides or semiconductor substrates.

Other suitable piezoresistive and temperature sensing materials and methods of deposition are described in U.S. Pat. No. 4,994,781 and 5,088,329 to Sahagen. These patents are hereby incorporated by reference.

As shown in FIG. 3, the connecting arms 76, the contact pads 78, the piezoresistive elements 12 and the temperature sensitive elements 11 can be made of similar material. For example, sapphire can provide a bandpass filter transparent to electromagnetic waves of wave lengths ranging from 0.15 microns to 6 microns.

Piezoresistive elements 12 in a Wheatstone bridge are disposed on the first major surface 80 (FIG. 2) of the diaphragm 1 facing toward the cavity 66. The fluid medium exerts pressure on the second major surface 82 (FIG. 2) of diaphragm 1 causing the diaphragm 1 to flex toward the cavity 66. When the voltage across the Wheatstone bridge is constant the flexing of the diaphragm 1 produces a change in the electrical current.

Figure 5:
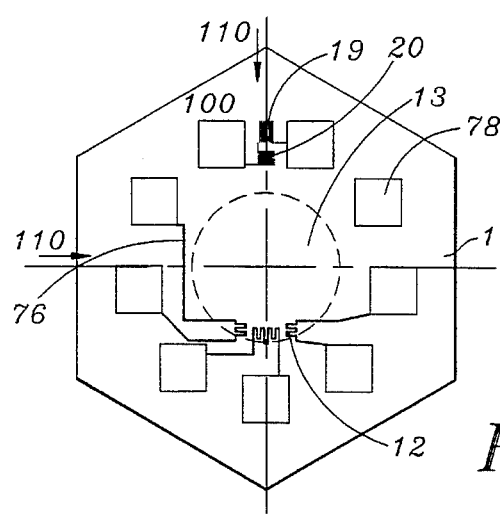
FIG. 5 illustrates an embodiment of the diaphragm and an arrangement of the contact pads, the connecting arms, the piezoresistive elements in a Wheatstone bridge and an arrangement of the temperature sensing elements to reduce residual pressure sensitivity.

As shown in FIG. 5, the electrical signal is conducted through the resistive connecting arms 76 to the contact pads 78. The pads 78 are welded to leads (not shown) and threaded through holes 3 (FIG. 2). The leads carry the electrical signal to the outside world. The temperature sensitive elements 19 and 20 are located on a supported part of the diaphragm 1 where there is essentially no flexing. Thus, a temperature change will produce a ratiometric electrical signal change which is again transferred to external world for analysis through the leads described above.

FIG. 5 illustrates an embodiment where an electromagnetically transparent window 13 is centrally located in diaphragm 1. Alternatively, the window 13 can be located at another part of the diaphragm 1 or opposite a hole 3 (FIG. 1) capable of containing at least one fiber optic.

FIG. 5 illustrates a diaphragm 1 without fiber optics when only pressure and temperature measurements are desired. The piezoresistive elements 12 are arranged in a Wheatstone bridge and located in the cavity 66 on an unsupported area of the first major surface 80 (FIG. 2) of the diaphragm 1 as illustrated. As an alternative, the piezoresistive elements 12 are arranged anywhere on the first major surface 80.

The temperature sensitive elements 19 and 20 are arranged in a Wheatstone bridge on a supported part of the first major surface 80 of diaphragm 1. In an alternative embodiment, the temperature sensitive elements 19 and 20 are disposed anywhere on first major surface 80 (FIG. 2).

It is preferred to place the temperature sensitive elements 19 and 20 where there is essentially no flexing of the diaphragm 1. In this embodiment, the temperature elements 19 and 20 will be virtually insensitive to pressure exerted on the diaphragm 1. Yet, even at this location, residual stress may still affect the accuracy of the temperature monitoring function of the probe 60.

FIG. 3 illustrates an arrangement of the temperature elements 11 which will reduce or eliminate residual stress. The temperature sensitive elements 11 are arranged along a 45° angle with respect to the 110 crystallographic axes of silicon.

FIG. 5 illustrates another embodiment to minimize the residual pressure sensitivity of the temperature sensitive elements 19 and 20. The temperature sensitive elements 19 and 20 are arranged to be in series and perpendicular to each other in a 100 crystallographic plane along the 110 axes on a supported area of the diaphragm 1. Although the temperature sensitive elements 19 and 20 will be still independently sensitive to minute residual stresses, the stress magnitudes are equal, opposite and cancel out and resulting in residual stress insensitivity.

FIG. 6 illustrates another embodiment having a sleeve 9 to strengthen the probe 60. Sleeve 9 strengthens the base 2 by eliminating the breakage of a sometime brittle base 2 and/or high pressure exerted by the fluid medium on the base 2.

FIG. 6 illustrates a electromagnetic window arrangement. A plurality of holes 3 of the base 2 extend from the upper surface 62 to the lower surface 64. As shown in FIG. 6, each hole 3 can hold at least one fiber optic pair 31 and 32 to perform independent monitoring and analysis of the fluid medium through electromagnetic waves. Diaphragm 1 (e.g., of sapphire) is bonded to base 2 as discussed before. The diaphragm 1 provides a plurality of electromagnetic wave windows to seal off holes 3. The windows seal off the upper surface 62 of the base 2. The ends of the fiber optics 31 and 32 make intimate contact with diaphragm 1. Waves incident on the fluid medium in intimate contact with second major surface 82 of diaphragm 1 are reflected and collected through fiber optic 32 for analytical and other purposes.

FIG. 6A is an end view of the probe of FIG. 6 viewed from the fluid medium side taken on line A—A. FIG. 6A also illustrates additional electromagnetic windows located opposite and aligned with holes, wherein the source and collector fiber optics are used to measure temperature of the fluid medium.

FIG. 6B is a close up view of section B of FIG. 6 indicating the cone shaped ends of the fiber optic pairs.

As shown in FIG. 6 and 6E, similar results can be achieved by installing or depositing bandpass filters 102 inside each hole 3 of base 2 between the ends of fiber optic 31 and 32 and diaphragm 1 or at any other convenient location. For example, the bandpass filter(s) 102 can be placed anywhere between the electromagnetic source and the fluid medium being monitored. Such bandpass filters will help to identify the absorption/transmission curve at the select bandwidths.

As shown in FIG. 6E, the present invention also provides an embodiment to collect reflected or scattered electromagnetic waves which are focused on a temperature sensitive element 104 on the first major surface 80 of the diaphragm 1. The electromagnetic waves, particularly those in the infrared range, incident on temperature sensitive elements 104 will release additional free electrons which will change the resistance in proportion to the intensity of the incident waves which in turn will detect certain characteristics of the fluid medium such as the composition or identify specific elements, compounds and/or mixtures of the fluid medium. This particular embodiment should have broad application to the automotive industry, for example, as a pollution detector as well as in other industries requiring a relatively inexpensive probe for precise composition analysis of a fluid medium.

FIG. 6C is a close up end view of an embodiment of the fiber optic pair taken at section B of FIG. 6.

FIG. 6D is a close up end view of an alternative embodiment of fiber optic pair taken at section B of FIG. 6.

The embodiment shown in FIG. 6 provides means to target specific elements, compounds or mixtures in a fluid medium by employing bandpass filters such that the concentration in the fluid medium can be determined. This embodiment can have application as a cost effective compact pollution detector for use in the automotive industry. Of course, the embodiment has numerous other applications wherever the quantitative and qualitative analysis of elements, compounds or mixtures is required.

Figure 7:
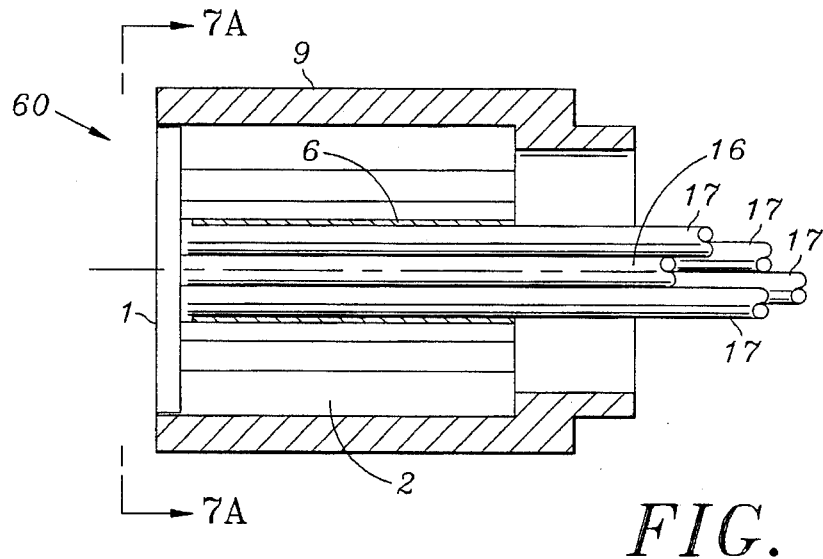
FIG. 7 is a cross-section through an embodiment of the probe employing multifiber optics and a sleeve which strengthens the probe.

FIG. 7 is a cross-section through an embodiment of the probe 60 employing multifiber optics 16 and 17 and a sleeve 9 housing the base 2 to strengthen the probe 60. In this embodiment, a fiber optic 16 emits waves into the fluid medium and a plurality of the fiber optics 17 positioned around fiber optic 16 collect waves after interaction with the fluid medium. Although this multifiber optic embodiment offers vast improvement over a single fiber optic collector, it still lacks the collection efficiency necessary to perform certain tasks with a Raman spectrometer and other spectrometers.

Figure 7A:
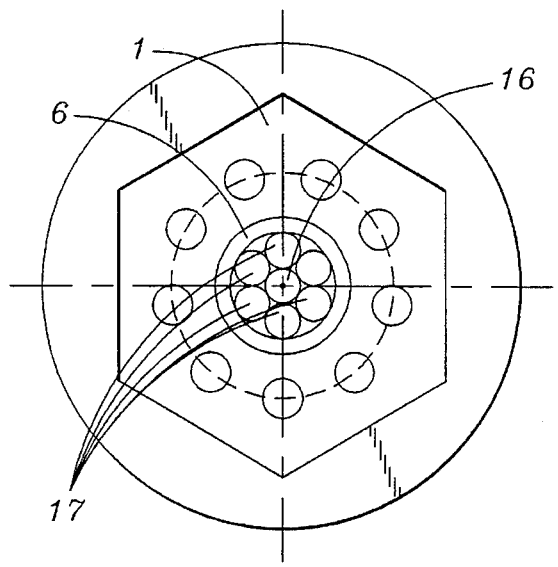
FIG. 7A is an end view of the probe of FIG. 7 taken from the fluid medium along line A—A of FIG. 7.

FIG. 7A is an end view of the probe 60 of FIG. 7 and further illustrates the relative locations of the diaphragm 1, the source fiber optic 16 and the collecting fiber optics 17 and a liner 6.

Figure 7B:
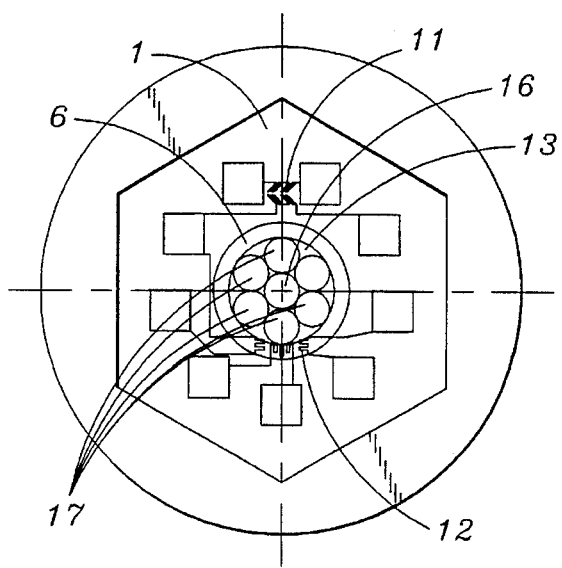
FIG. 7B is an end view of the probe of FIG. 7. It illustrates the locations of a diaphragm, the source fiber optic, the collecting fiber optics, the temperature sensitive elements and the piezoresistive pressure elements on the diaphragm.

FIG. 7B further illustrates an end view of probe 60 shown in FIG. 7 and the location of the temperature sensitive elements 11 and piezoresistive elements 12. The pressure, temperature, composition probe 60 can be used either in combination to monitor these parameters simultaneously or individually or in some combination.

Figure 1:
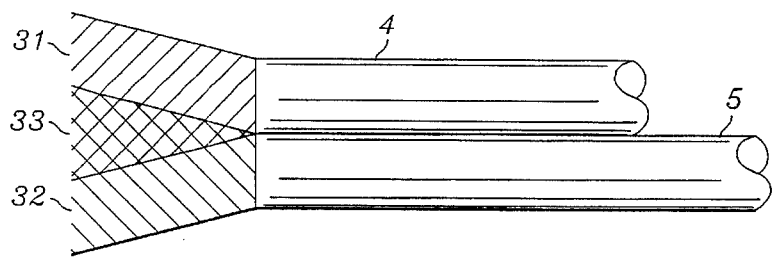
FIG. 1 illustrates the limitations of a conventional fiber optic pair.
Figure 8:
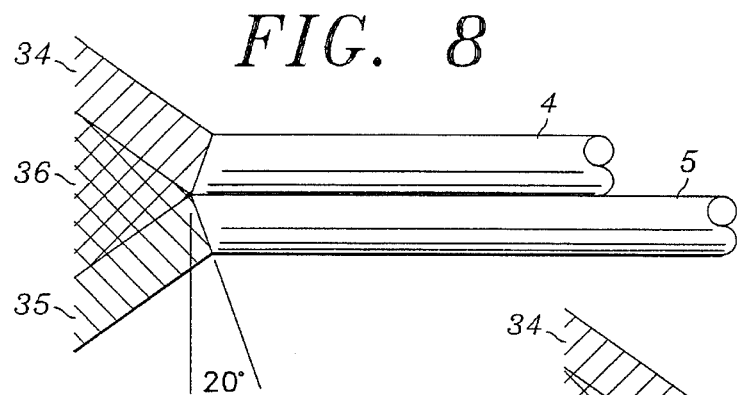
FIG. 8 illustrates an embodiment of a fiber optic pair having a cone-shape end and a larger grazing field than the conventional fiber optic pair of FIG. 1.

FIG. 8 illustrates a fiber optic pair having a cone-shape end and a grazing field larger than a conventional fiber optic pair as shown in FIG. 1. As shown in FIG. 8, in this embodiment, the present invention increases the individual acceptance cones 34 and 35 to increase the grazing field 36 for higher collection efficiency.

FIG. 8 illustrates the source fiber optic 4 and the collecting fiber optic 5 having a cone-shaped end defining an angle of approximately 20° with respect to a plane perpendicular to the fiber optic axis. Favorable results can be achieved when the angle is about 20° but the angle can be anywhere from about 5° to about 45°. The only requirement is that the maximum angle should be no greater than the critical angle of the fiber optic employed.

FIG. 8 illustrates a technique to dramatically improve collection efficiency without additional fiber optics beyond the original fiber optic pair and without increasing their individual diameters. Thus, the present invention provides improved collection efficiency over that of a conventional fiber optic pair shown in FIG. 1.

Figure 9:
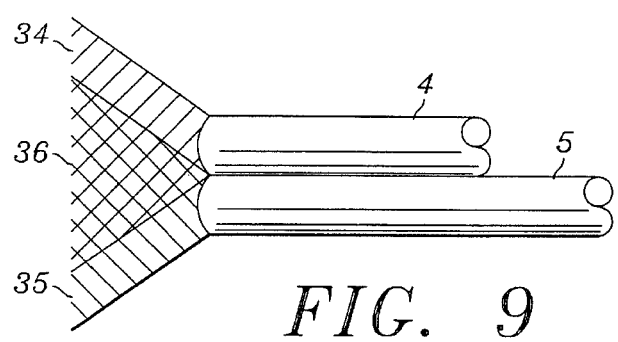
FIG. 9 illustrates an embodiment of a fiber optic pair where each fiber optic has a convex end.

FIG. 9 illustrates a fiber optic pair 4 and 5 where each fiber optic has a convex end. In one embodiment, the fiber optic ends are convex, spherical and have a focal length greater than the diameter of the fiber optic. The convex ends improves the coverage of the grazing field 36 by increasing acceptance cone 34 and 35 overlap. FIG. 9 provides a fiber optic pair with improved collection efficiency over that of a conventional fiber optic pair of the same size, shape, material, diameter and arrangement.

Figure 10:
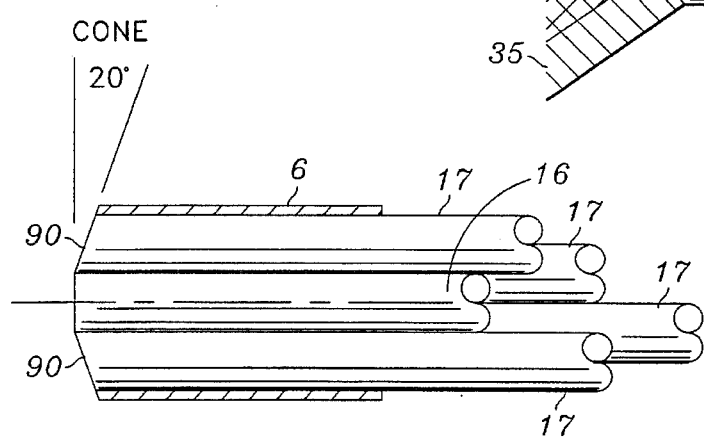
FIG. 10 illustrates an embodiment of a multifiber optic having a truncated cone shaped end.

FIG. 10 illustrates a multifiber optic arrangement having a truncated cone shaped end. In one embodiment, the source fiber optic 16 is central to a plurality of collecting fiber optics 17. A liner 6 houses the multifiber optics.

In this embodiment, each end 90 of the collecting fiber optics 17 defines a 20° angle with respect to a plane perpendicular to the axis of the source fiber optic 16. Yet, the angle can be anywhere from about 5° to 45° and even up to the critical angle of the fiber optic. This embodiment also improves the coverage of the grazing field.

Figure 11:
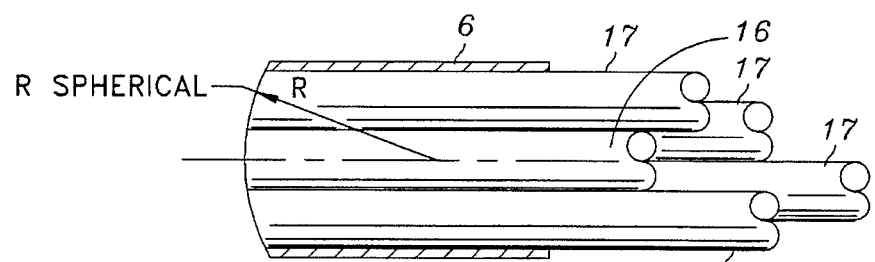
FIG. 11 illustrates an embodiment of a multifiber optic having a spherical shaped end.

FIG. 11 illustrates another multifiber optic arrangement having a spherical shaped end. In this embodiment, the source fiber optic 16 is central to a plurality of collecting fiber optics 17. The collecting fiber optics 17 are arranged about the source fiber optic 16 similar to that shown in FIG. 10. The fiber optics 16 and 17 ends terminate in a spherical shape of radius R. This embodiment will improve the coverage of the grazing field (and collection efficiency) over that of conventional fiber optics using the same arrangement and fibers of similar size, shape, material and diameter. A liner 6 houses the multifiber optics.

Figure 12:
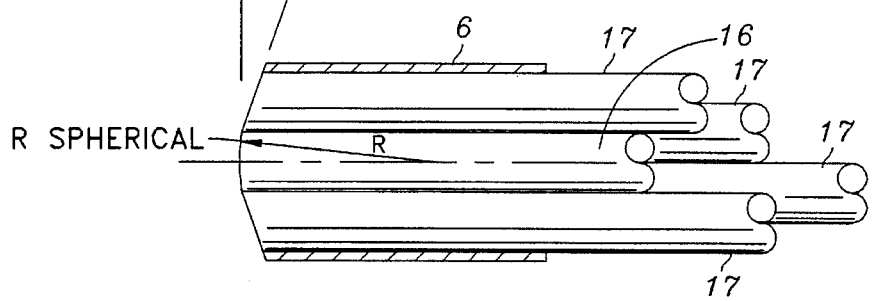
FIG. 12 illustrates an embodiment of a multifiber optic having a center fiber optic having a spherical shape end and a plurality of surrounding fiber optics having cone shaped ends.

FIG. 12 illustrates a multifiber optic embodiment where the source fiber optic 16 is in the center of a plurality of collecting fiber optics 17. The source fiber optic 16 has a spherical shaped end of radius R. The collecting fiber optics 17 are arranged about the source fiber optic 16. Each collecting fiber optic 17 defines an angle of about 20° or an angle anywhere from about 5° to about 45° with respect to a plane perpendicular to the fiber optic axis. This embodiment of the fiber optic ends will improve the grazing field (and collection efficiency) over the same number of conventional fiber optics of similar size, shape, material and diameter. The fiber optic ends can be modified by conventional techniques including grinding, lapping and polishing.

FIG. 13 illustrates a multifiber optic arrangement having a cone shaped end. In one embodiment, the source fiber optic 16 is central to collecting fiber optics 17 arranged about the periphery in a manner similar to that shown in FIG. 10. The fiber optics 16 and 17 ends terminate in a cone with an angle of about 20° with respect to a plane perpendicular to the center fiber optic axis, or at any angle mentioned earlier with respect to FIG. 10. This modification of the fiber optic ends will also increase the grazing field (and collection efficiency) over that of conventional fiber optics employing the same number of fibers of similar size, shape, material, diameter and embodiment.

FIGS. 14A and 14B clarify the advantages of the present invention attained through embodiments illustrated in FIGS. 8, 10, 12 and 13. As shown in FIG. 14A, a fiber optic pair having conventional ends has a grazing field of about 30°. In contrast, a fiber optic pair (FIG. 14B) having cone shaped ends with an angle of about 15° with respect to a plane perpendicular to the fiber optic axis has a grazing field of about 60°.

FIGS. 15A and 15B illustrate an advantage of using square fiber optics versus round fiber optics. The square fiber optics (FIG. 15A) provide a larger grazing field (i.e., the shaded area=0.237 sq. in.) than the round fiber optics (FIG. 15B) grazing field (i.e., the shaded area=0.221 sq. in.)

Figure 16:
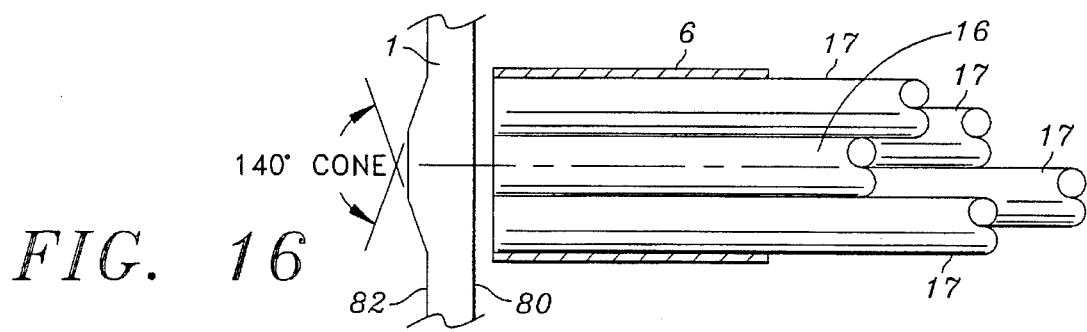
FIG. 16 illustrates a diaphragm having a cone side and a flat side which can mate with conventional fiber optic ends.

FIG. 16 illustrates another embodiment where the first major surface 80 of the diaphragm 1 is flat to mate with the ends of the ends of conventional fiber optics 16 and 17 and the second major surface 82 is a 140° cone. FIG. 16 also illustrates a liner 6. Based on the foregoing discussion relating to increasing the grazing field, it follows that improved electromagnetic wave collection will result.

Figure 17:
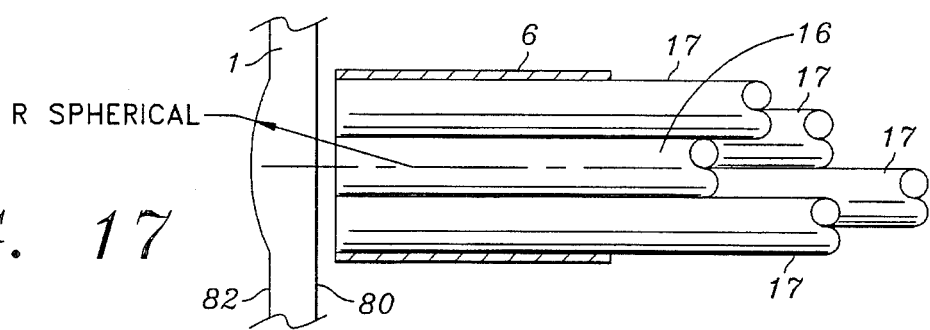
FIG. 17 illustrates a diaphragm having a spherical side and a flat side which can mate with conventional fiber optic ends.
Figure 18:
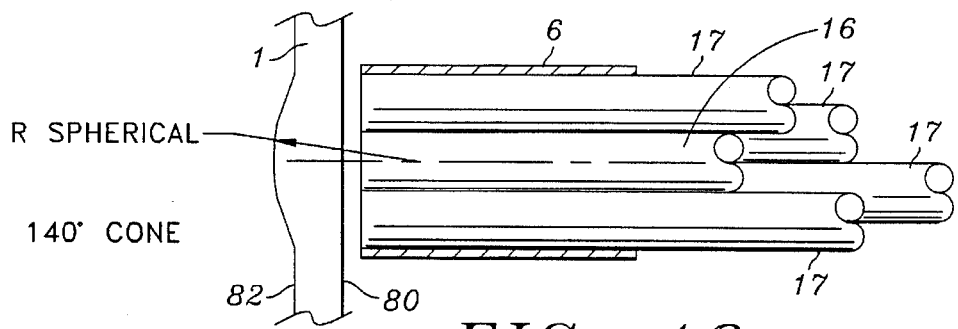
FIG. 18 illustrates a diaphragm having a spherical center and cone annulus side and a flat side which can mate with conventional fiber optic ends.
Figure 19:
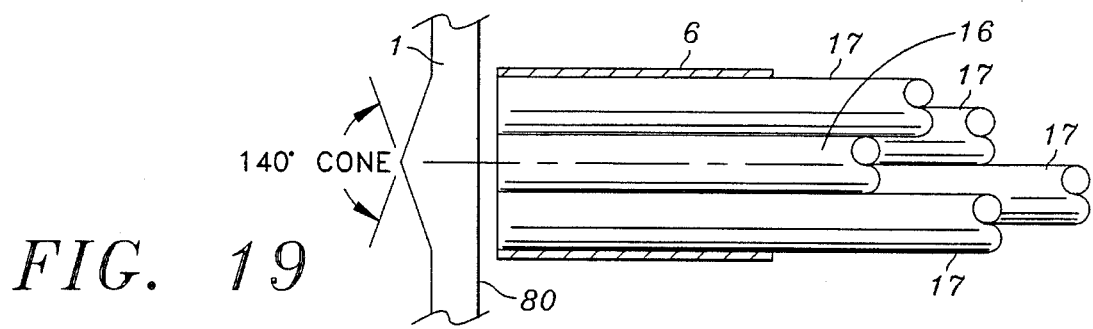
FIG. 19 illustrates a diaphragm having a cone side and a flat side which can mate with conventional fiber optic ends and a location for a liner.
Figure 20:
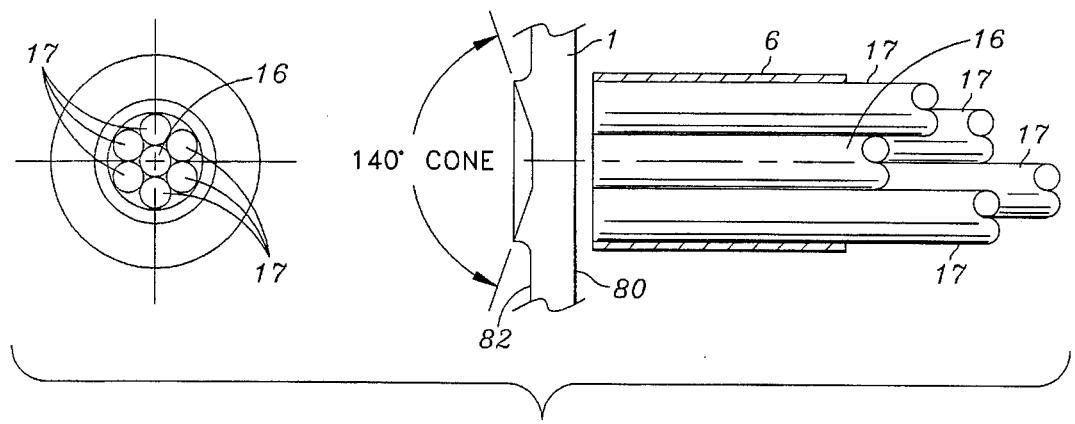
FIG. 20 illustrates a diaphragm having a concave side and a flat side which can mate with conventional fiber optic ends and a location for a liner.

FIGS. 17, 18 and 19 illustrate still other embodiments where the first major surface 80 of the diaphragm 1 can mate with the ends of conventional fiber optics 16 and 17. The diaphragm 1 has a second major surface 82 of respectively a spherical shape of radius R (FIG. 17), a partial spherical shape of radius R in the center and a peripheral cone shaped annulus of 140° (FIG. 18), a cone shape of 140° (FIG. 19), a concave cone periphery of 140° (FIG. 20) for improved electromagnetic collection efficiencies. The cone shaped diaphragms 1 may define an angle anywhere from 5° to 45° and no greater than the critical angle with respect to a plane perpendicular to the fiber optic axis. FIGS. 17, 18, 19 and 20 also illustrate a liner 6.

Figure 21:
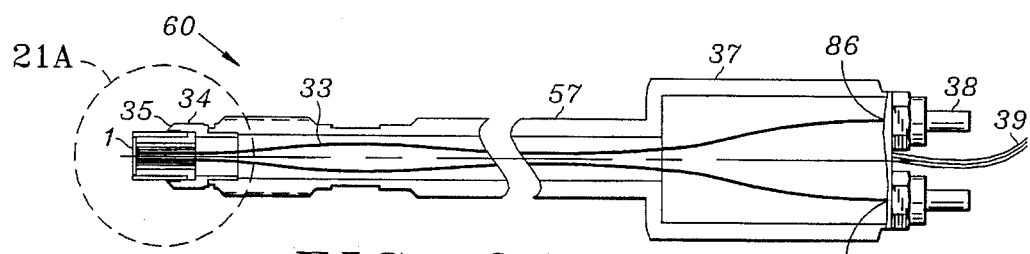
FIG. 21 illustrates an assembly of the probe and the location of the fiber optics in the assembly.
Figure 21A:
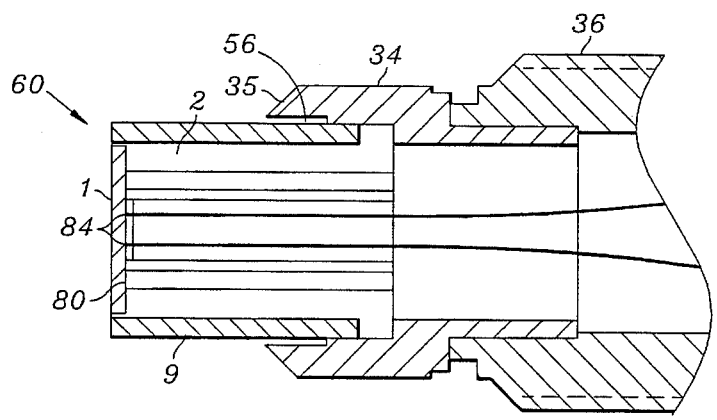
FIG. 21A is a close up of section A of FIG. 21 illustrating a means to isolate the probe from a fluid medium.

FIG. 21 illustrates an assembly of the probe 60 and the location of fiber optic pair within the assembly. As shown in FIG. 21 or 21A, the probe 60 includes a diaphragm 1, a pressure cell base 2, a sleeve 9 and a hollow ring 34. The hollow ring 34 includes a sealing tip 35 at an end with a 45° angle with respect to the sleeve 9. The hollow ring 34 forms an isolation slot 56 and is integral or attaches to body 36 which is integral with upper housing 37. The upper housing 37 terminates at plate 92 where connectors 38 are provided. The connectors 38 couple the fiber optics 4 and 5 to the outside world. Protective cable 39 includes insulated wires connected to temperature sensitive elements 11 and piezoresistive elements 12 (FIGS. 3 and 5) through their bonded leads (not shown) so that an analog output ratiometric to fluid medium pressure and temperature can be obtained.

FIG. 21 illustrates an approach to maintaining the ends of the fiber optic pair 33 and the diaphragm 1 (FIG. 21A) in intimate contact with each other. As shown in FIGS. 21 and 21A, the ends 84 of the fiber optics 33 make intimate contact with the first major surface 80 of diaphragm 1. Opposite ends 86 of the fiber optics 33 attach to connectors 38. The fiber optics 33 have slack and are resilient. Because of their resiliency, they are held in compression in the probe 60. Thus, any thermal expansion of the overall package of the probe 60 will cause the resilient fiber optics 33 to extend to the new expanded length of the probe 60 such that they maintain intimate contact with the diaphragm 1. Furthermore, any thermal contraction of the probe 60 will cause the fiber optics 33 to be compressed. In either event, the fiber optics 33 are maintained in intimate contact with diaphragm 1. This approach eliminates the separation of the diaphragm 1 from the ends 84 of fiber optics 33 from either temperature change or flexing of the diaphragm 1. This is important because analysis cannot be reliable unless the ends 84 of fiber optics 33 and diaphragm 1 maintain intimate contact or stay a fixed distance apart.

FIG. 21A is a close up of section A of the probe depicted in FIG. 21 which illustrates the relationship of the hollow ring 34, the body 36, the base 2, the diaphragm 1, the sleeve 9 and the sealing tip 35 and the isolation slot 56 which isolate the probe 60 from high temperature and pressure, corrosive and hostile fluid medium and transference of stress when the probe 60 is installed in the field.

Figure 22:
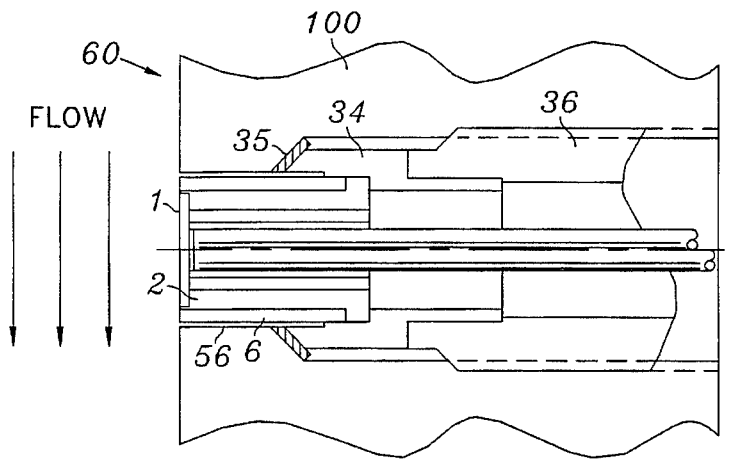
FIG. 22 illustrates a probe in the fluid medium and an isolation slot.

FIG. 22 illustrates an approach to isolate diaphragm 1 from any stress which might prevent affect the accuracy of the probe. FIG. 22 shows a beveled sealing tip 35 of the probe 60 and an isolation slot 56. Isolation slot 56 is also shown in FIG. 21A. The sealing tip 35 isolates the diaphragm 1 of the probe 60 from the fluid medium. Body 36 has threads which exert a longitudinal force when tip 35 makes contact with the female beveled seal 36 of the housing 100. A compressive longitudinal force exerted on both beveled surfaces which is sufficient to seal the probe 60 from the outside world will also produce residual stress on the diaphragm 1. Isolation slot 56 reduces or eliminates stress from being transferred to the diaphragm 1.

Figure 23:
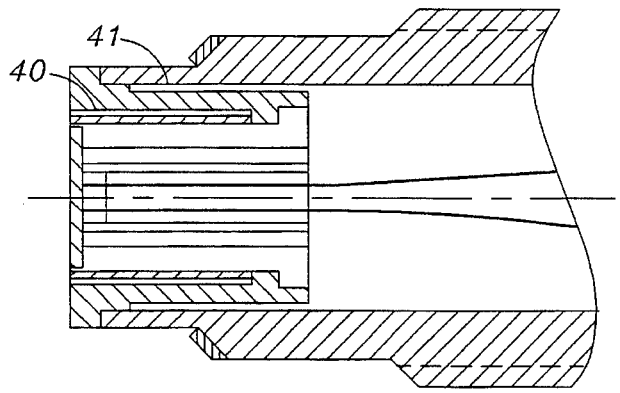
FIG. 23 illustrates an embodiment having a double isolation slot to reduce residual stress on the diaphragm.

FIG. 23 is another embodiment employing a double isolation slot. The isolation slot 40 coupled with isolation slot 41 further reduces the transfer of residual stress to diaphragm 1. Additional isolation slots (not shown) can be employed if desired to further reduce any residual stress.

Figure 24:
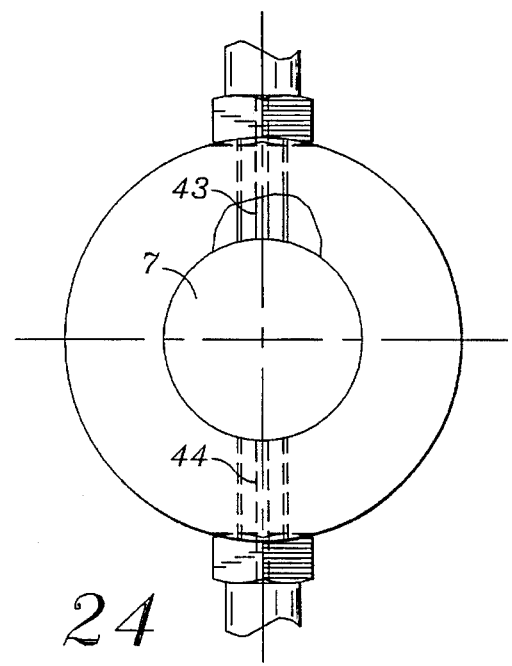
FIG. 24 illustrates another application where two probes face each other in a fluid medium chamber.

FIG. 24 illustrates another application where two independent probes 43 and 44 are engaged to face each other in a cylindrical fluid medium chamber 7. Probe 43 acts as a source fiber optic and probe 44 as the collecting fiber optic. This embodiment is ideal, for example, in the automotive industry where real-time on-line exhaust gas analysis is essential for smog control.

Figure 25:
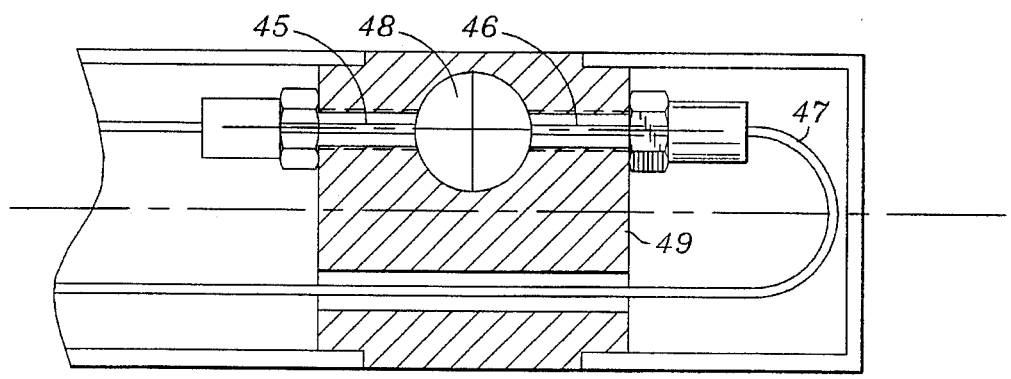
FIG. 25 illustrates a transmission inefficiency associated with a compact two-probe embodiment when fiber optics take a sharp turn.

FIG. 25 illustrates a problem with the compact two-probe embodiments. FIG. 25 shows two probe as depicted in FIG. 2 which are engaged in a body 49. Probe 45 is the emitter probe and probe 46 is the collector probe. A "U" turn 47 in the fiber optics returns to the signal from the collector probe 46 to the outside world. The general arrangement of the probes 45 and 46 and the fluid medium chamber 48 will render this two probe embodiment compact. However, the compact nature of this two-probe design has the distinct disadvantage that the collector fiber optic is forced into making a "sharp U" turn 47 which sacrifices transmission efficiency.

Figure 26:
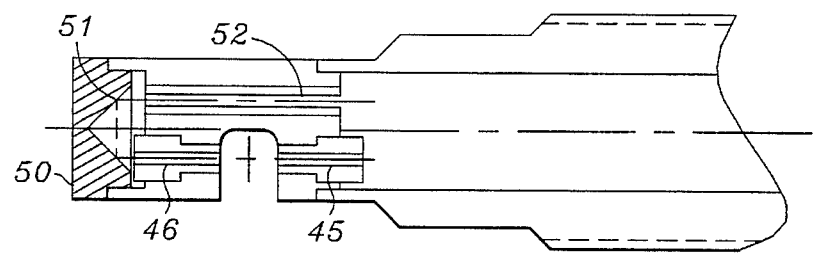
FIG. 26 illustrates a V-shaped or spherical shaped reflector which eliminates transmission inefficiency when fiber optics are required to take a sharp turn.

FIG. 26 illustrates another aspect of the present invention which eliminates this transmission inefficiency. In an embodiment, the present invention provides a V-shaped or spherical shape electromagnetic reflector 51 disposed in a body 50 and symmetrically opposite two fiber optics 46 and 52. This embodiment provides a compact package which renders a miniature two-probe transmission efficient. When the surface of the reflector 51 mounted in body 50 of the probe is coated with electromagnetic wave reflective material, such as gold, silver, rhodium and nickel, the transmission efficiency may be greater than 30%.

Figure 27:
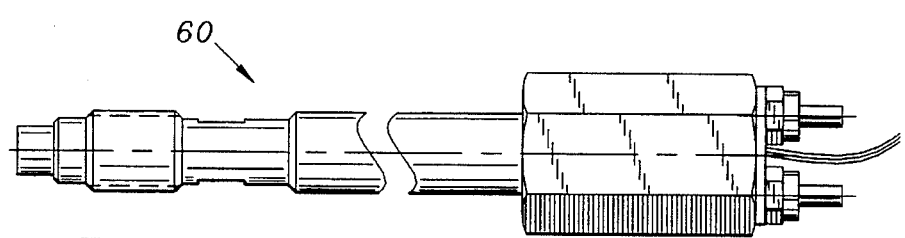
FIG. 27 illustrates the overall package for the probe of the present invention.

FIG. 27 illustrates the overall package for the probe 60 of the present invention.

Figure 28:
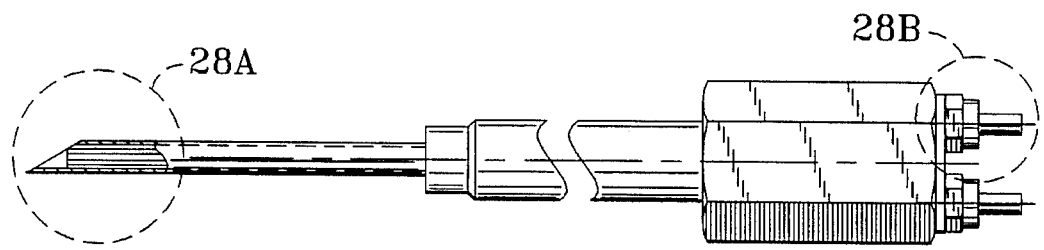
FIG. 28 illustrates an embodiment of the probe where at least one fiber optic is housed in a hypodermic-like housing for medical applications.
Figure 28A:
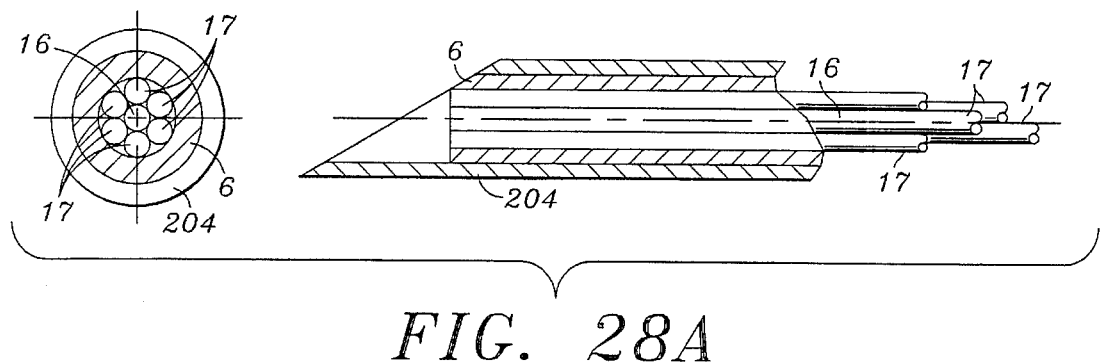
FIG. 28A illustrates the details of the hypodermic needle taken at section A of FIG. 28.

FIG. 28 illustrates still another embodiment of a miniaturized probe 60 for medical applications having at least one fiber optic housed in a sleeve forming a hypodermic-needle. As shown in FIG. 28A, in one embodiment, the probe 60 includes a plurality of fiber optics 16 and 17 which are housed in a liner 6 which is housed in a sleeve 204. The sleeve 204 forms a hypodermic needle for in-vivo medical application and strengthens the probe 60. Fiber optic 16 emits electromagnetic waves into the fluid medium and fiber optic 17 collects the scattered, luminescence or dispersed waves and transmits them to the external world for analysis as before. The probe 60 can be of similar types of materials and construction as the probe 60 of FIG. 2 as long as the material is not deleterious to the patient. The probe 60 may find application in real-time on-line monitoring of blood, bioreactors, abnormal cell growth and other medical applications.

Figure 28B:
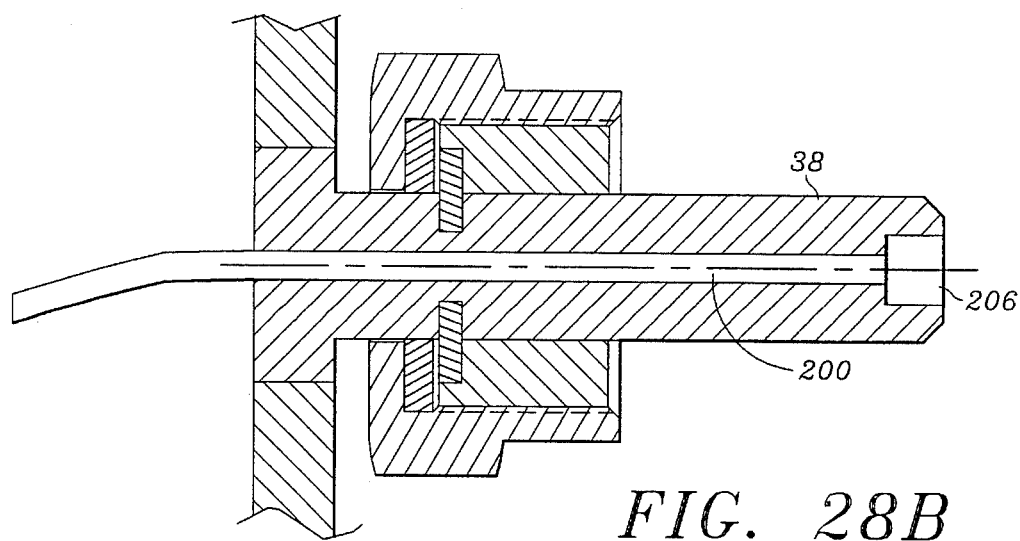
FIG. 28B illustrates the details taken at section B of FIG. 28 where one end of a fiber optic tube opposite the hypodermic needle end is sealed by a window to form a vacuum or gas filled chamber.

FIG. 28B is a close up of section B of FIG. 28 showing a connection for a fiber optic tube 200. The tube 200 is connected exits the probe 60 through connector 38 and is sealed by window 206 to form a vacuum or gas filled chamber.

Figure 29:
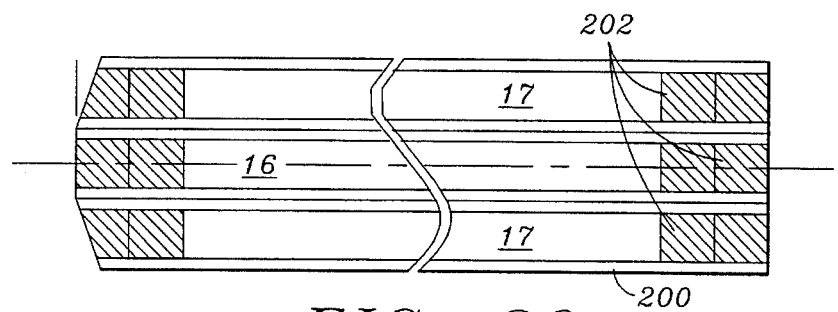
FIG. 29 illustrates the construction of a fiber optic tube making broad electromagnetic wavelength range transmission possible.

FIG. 29 illustrates at least one fiber optic tube 200 capable of transmitting a broad electromagnetic wavelength range. Crystalline or amorphous refractory, metal oxides, semiconductor material, or intermetallics, and plastic can be used to make the tube 200. Favorable results can be achieved when the inner diameter of the tube 200 is about 500 microns and the outer diameter about 600 microns. The ends of the tube 200 can be either left open or sealed with windows 202 and can assume the modified fiber optic ends of FIGS. 6B, 8, 9–13, 14B and 16–20. for example, the windows 202 shown in FIG. 29 form a cone shape derived from a cut across the end of the window such that when it is installed in the tube the end of the window makes an angle of about 20° with respect to a plane perpendicular with the fiber optic axis. When windows 202 properly seal off the tube 200 at both ends, the tube 200 can be filled with an inert gas or preferably placed under a vacuum. Alternatively, the tube 200 exits the probe 60 through connector 38 and is sealed by window 206 to form a vacuum or gas filled chamber.

The wall of tube 200 can be made of sapphire, quartz, glass, plastics or any other material suitable for reflecting the electromagnetic waves and having refractive index greater than 1.00. The fiber optic tube has the capability of transmitting electromagnetic waves covering virtually the entire wavelength range from gamma waves, x-rays, infrared, ultra-violet and other wavelengths. In the embodiment using a vacuum, the only real limit to a broad wavelength transmission is the material being used for the windows 202 or 206.

For example, the fiber optics 16 and 17 can be used to detect cancer cells in the human body and x-ray or other waves transmitted through a fiber optic such as tube 200 for treatment of the same cancer cells. The fiber optic tube described in connection with FIG. 29 may be particularly suitable for the transmission of x-rays, gamma rays or other radiation capable of eradicating undesirable cells. The combination of such novel features will make it possible to monitor the eradication or growth rate and status of undesirable cells simultaneous with the irradiation treatment.

The embodiment described in FIG. 29 provides an added advantage that, unlike hollow metal tubes, the curving of the long fiber optics produced with the present invention will no longer drastically limit the transmission efficiency of the fiber optic.

A metal tube with polished inner walls and plated with gold, silver, platinum, rhodium, or nickel with greater than 70% reflectivity efficiency can be used. However, a great deal of transmission efficiency will be lost due to the incompatibility of the refractive index. Because the slightest curve in tube 200 will curtail or substantially stop any electromagnetic wave transmission.

What is claimed is:

1. A probe for monitoring a fluid pressure, temperature and composition, simultaneously or separately, comprising:

a base having an upper and lower surface, a cavity located along the upper surface, at least one hole extending from the upper to the lower surface;

at least one fiber optic, in the hole, for transmitting an electromagnetic wave;

a diaphragm having a first and second major surface, the first major surface facing the upper surface and the second major surface facing the fluid, wherein the pressure of the fluid is applied in a direction that causes the diaphragm to flex toward the cavity and wherein the diaphragm is capable of transmitting the electromagnetic wave;

a pressure sensitive element on the diaphragm; and a temperature sensitive element on the diaphragm.

2. The probe of claim 1, wherein the base comprises material selected from the group consisting of an amorphous metal oxide, a crystalline metal oxide, a semiconductor material, a metal, and a metal alloy, or a combination thereof, the material having a temperature coefficient of expansion of $1\times10^{-7}/°$ F. to about $2\times10^{-5}/°$ F.

3. The probe of claim 1, wherein the base comprises material selected from the group consisting of alumina, diamond, diamond-like material, quartz, beryllium oxide, silicon nitride, silicon carbide compounds, brylia and alumina, MgO and $Al_2O_3$ compounds, zirconium oxide and aluminum oxide systems, $SiO_2$ and aluminum compounds, and silicon nitrate and aluminum oxide compound, or a combination thereof, the material having a temperature coefficient of expansion of $1\times10^{-7}/°$ F. to about $2\times10^{-5}/°$ F.

4. The probe of claim 1, wherein the diaphragm comprises material selected from the group consisting of an amorphous metal oxide, a crystalline metal oxide, a semiconductor material, intermetallics, and a metal, or a combination thereof, the material having a temperature coefficient of expansion of $1\times10^{-7}/°$ F. to about $2\times10^{5}/°$ F.

5. The probe of claim 1, wherein the diaphragm comprises material selected from the group consisting of single crystalline sapphire, polycrystalline sapphire, diamond, diamond-like material, quartz, alumina, beryllium oxide, silicon nitride, silicon carbide compounds, brylia and alumina, MgO and $Al_2O_3$ compounds, zirconium oxide and alumina oxide systems, $SiO_2$ and alumina compounds, and silicon nitrate and aluminum oxide compounds, or a combination thereof, the material having a temperature coefficient of expansion of $1\times10^{7}/°$ F. to about $2\times10^{-5}/°$ F.

6. The probe of claim 1, wherein the fiber optic includes a cladding and a core, wherein the cladding comprises material selected from the group consisting of diamond, diamond-like material, and sapphire, or a combination thereof.

7. The probe of claim 1, wherein the at least one fiber optic comprises one fiber optic surrounded by a plurality of fiber optics.

8. The probe of claim 7, wherein the one fiber optic emits the electromagnetic wave and the plurality of fiber optics collect the electromagnetic wave after interaction with the fluid.

9. The probe of claim 7, wherein the one fiber optic collects the electromagnetic wave after interaction with the fluid and the plurality of fiber optics emit the electromagnetic wave.

10. The probe of claim 6, 7, 8 or 9, further comprising a sleeve housing and strengthening the base.

11. The probe of claim 1, further comprising a bonding layer between the diaphragm and the base, wherein the bonding layer comprises material selected from the group consisting of a glass ceramic, a glass, a metal oxide, and a brazing material, the material having a temperature coefficient of expansion of $1\times10^{-7}/°$ F. to about $2\times10^{-5}/°$ F.

12. The probe of claim 1, wherein the diaphragm is a single crystalline material having a 100 plane and crystallographic axis of 110 and wherein the temperature sensitive element is disposed on the 100 plane of the diaphragm and includes a longitudinal axis defining a 45 degree angle with respect to the 110 crystallographic axis.

13. The probe of claim 1, wherein the diaphragm is a single crystalline diaphragm having a 100 plane and crystallographic axis of 110, wherein the temperature sensitive element includes:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis defining a 90 degree angle with respect to the 110 axis.

14. A probe for monitoring a fluid medium, comprising:

a base having an upper surface and a lower surface, and at least one hole extending from the upper to the lower surface;

at least one fiber optic, in the hole, for transmitting an electromagnetic wave; and a window having a first and second major surface, the window mounted on the base, the first major surface facing the upper surface and the second major surface facing the fluid medium, wherein a fluid pressure of the fluid medium is applied in a direction that causes the window to flex toward the base and wherein the window is capable of transmitting an electromagnetic wave.

15. The probe of claim 14, wherein the base comprises material selected from the group consisting of an amorphous metal oxide, a crystalline metal oxide, a semiconductor material, a metal, and a metal alloy, or a combination thereof, the material having a temperature coefficient of expansion of $1\times10^{-7}/°$ F. to about $2\times10^{-5}/°$ F.

16. The probe of claim 14, wherein the base comprises material selected from the group consisting of alumina, diamond, diamond-like material, quartz, beryllium oxide, silicon nitride, silicon carbide compounds, brylia and alumina, MgO and $Al_2O_3$ compounds, zirconium oxide and aluminum oxide systems, $SiO_2$ and aluminum compounds, and silicon nitrate and aluminum oxide compounds, or a combination thereof, the material having a temperature coefficient of expansion of $1\times10^{-7}/°$ F. to about $2\times10^{-5}/°$ F.

17. The probe of claim 14, wherein the window comprises material selected from the group consisting of an amorphous metal oxide, a crystalline metal oxide, a semiconductor material, intermetallics, and a metal, or a combination thereof, the material having a temperature coefficient of expansion of $1\times10^{-7}/°$ F. to about $2\times10^{-5}/°$ F.

18. The probe of claim 14, wherein the window comprises material selected from the group consisting of single crystalline sapphire, polycrystalline sapphire, diamond, quartz, alumina, beryllium oxide, silicon nitride, silicon carbide compounds, brylia and alumina, a MgO and $Al_2O_3$ compound, zirconium oxide and alumina oxide systems, $SiO_2$ and alumina compounds, and silicon nitrate and aluminum oxide compounds, or a combination thereof, the material having a temperature coefficient of expansion of $1\times10^{-7}/°$ F. to about $2\times10^{-5}/°$ F.

19. The probe of claim 14, 15, 16, 17 or 18, further comprising a sleeve housing the base and the window, wherein the sleeve strengthens the base and the window.

20. The probe of claim 14, further comprising a bonding layer between the window and the base, wherein the bonding layer comprises material selected from the group consisting of a glass ceramic, a glass, and a brazing material, the material having a temperature coefficient of expansion of $1\times10^{-7}/°$ F. to about $2\times10^{-5}/°$ F.

21. The probe of claim 14, wherein the fiber optic includes a cladding and a core, wherein the cladding comprises material selected from the group consisting of diamond and sapphire, or a combination thereof.

22. The probe of claim 14, further comprising at least one pressure sensitive element disposed on the window.

23. The probe of claim 14, further comprising at least one temperature sensitive element disposed on the window.

24. The probe of claim 14, wherein the window is a single crystalline material having a 100 plane and crystallographic axis of 110 and further comprising at least one temperature sensitive element having a longitudinal axis disposed on the 100 plane of the window and defining a 45 degree angle with respect to the 110 crystallographic axis.

25. The probe of claim 14, wherein the window is a single crystalline window having a 100 plane and crystallographic axis of 110 and further comprising:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis defining a 90 degree angle with respect to the 110 axis.

26. A probe for monitoring a fluid medium, comprising:

a base having an upper surface and a lower surface, a cavity located along the upper surface, and at least one hole extending from the upper to the lower surface for transmitting an electromagnetic wave;

a diaphragm having a first and second major surface, the first major surface facing the upper surface and the second major surface facing the fluid medium, wherein a fluid pressure of the fluid medium is applied in a direction that causes the diaphragm to flex toward the cavity;

at least one pressure sensitive element on the diaphragm; and a sleeve substantially housing and strengthening the base.

27. The probe of claim 26, wherein the sleeve comprises material selected from the group consisting of KOVAR, a nickel iron alloy, and a metal alloy, or a combination thereof, the material having a temperature coefficient of expansion of $1\times10^{-7}/°$ F. to about $2\times10^{-5}/°$ F.

28. The probe of claim 26, further comprising a bonding layer between the sleeve and the base, wherein the bonding layer comprises material selected from the group consisting of a glass ceramic, a glass, and a brazing material, the material having a temperature coefficient of expansion of $1\times10^{-7}/°$ F. to about $2\times10^{-5}/°$ F.

29. The probe of claim 28, wherein the sleeve, the base, and the bonding layer have substantially matching temperature coefficients of expansion.

30. The probe of claim 26, wherein the base comprises material selected from the group consisting of an amorphous metal oxide, a crystalline metal oxide, a semiconductor material, a metal, and a metal alloy, or a combination thereof, the material having a temperature coefficient of expansion of $1\times10^{-7}/°$ F. to about $2\times10^{-5}/°$ F.

31. The probe of claim 26, wherein the base comprises material selected from the group consisting of alumina, diamond, diamond-like material, quartz, beryllium oxide, silicon nitride, silicon carbide compounds, brylia and alumina, MgO and $Al_2O_3$ compounds, zirconium oxide and aluminum oxide systems, $SiO_2$ and aluminum oxide compounds, and silicon nitrate and aluminum oxide compounds, or a combination thereof, the material having a temperature coefficient of expansion of $1\times10^{-7}/°$ F. to about $2\times10^{-5}/°$ F.

32. The probe of claim 26, wherein the diaphragm comprises material selected from the group consisting of an amorphous metal oxide, a crystalline metal oxide, a semiconductor material, intermetallics, and a metal, or a combination thereof, the material having a temperature coefficient of expansion of $1\times10^{-7}/°$ F. to about $2\times10^{-5}/°$ F.

33. The probe of claim 26, wherein the diaphragm comprises material selected from the group consisting of single crystalline sapphire, polycrystalline sapphire, diamond, diamond-like material, quartz, alumina, beryllium oxide, silicon nitride, silicon carbide compounds, brylia and alumina, MgO and $Al_2O_3$ compounds, zirconium oxide and alumina oxide systems, $SiO_2$ and alumina compounds, and silicon nitrate and aluminum oxide compounds, or a combination thereof, the material having a temperature coefficient of expansion of $1\times10^{-7}/°$ F. to about $2\times10^{-5}/°$ F.

34. The probe of claim 26, further comprising a bonding layer between the diaphragm and the base, wherein the bonding layer comprises material selected from the group consisting of a glass ceramic, a glass, a metal oxide, and a brazing material, the material having a temperature coefficient of expansion of $1\times10^{-7}/°$ F. to about $2\times10^{-5}/°$ F.

35. The probe of claim 26, further comprising at least one temperature sensitive element on the diaphragm.

36. The probe of claim 35, wherein the diaphragm is a single crystalline diaphragm having a 100 plane and crystallographic axis of 110, wherein the at least one temperature sensitive element includes:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis which defines a 90 degree angle with respect to the 110 axis.

37. The probe of claim 26, wherein the diaphragm is a single crystalline material having a 100 plane and crystallographic axis of 110 and further comprising a temperature sensitive element disposed on the 100 plane of the diaphragm and including a longitudinal axis defining a 45 degree angle with respect to the 110 crystallographic axis.

38. A probe for monitoring a fluid medium comprising:

a base having an upper and a lower surface, and a plurality of holes extending from the upper to the lower surface;

at least one fiber optic in a hole of the plurality of holes; and means for sealing the plurality of holes and for transmitting an electromagnetic wave;

wherein the at least one fiber optic comprises a fiber optic pair capable of emitting the electromagnetic wave and collecting the electromagnetic wave after interaction with the fluid medium.

39. The probe of claim 38, wherein the ends of the fiber optic pair make intimate contact with the sealing means.

40. The probe of claim 38, wherein the sealing means includes a bonding layer between the fiber optic and at least one of the plurality of holes of the base.

41. The probe of claim 38, wherein the sealing means includes an individual window for each hole.

42. A probe for monitoring a fluid medium comprising:

a base having an upper and a lower surface, and a plurality of holes extending from the upper to the lower surface;

at least one fiber optic in a hole of the plurality of holes; and means for sealing the plurality of holes and for transmitting an electromagnetic wave;

wherein the sealing means includes a window covering all of the plurality of holes.

43. A probe for monitoring a fluid medium comprising:

a base having an upper and a lower surface, and a plurality of holes extending from the upper to the lower surface;

at least one fiber optic in a hole of the plurality of holes; and means for sealing the plurality of holes and for transmitting an electromagnetic wave;

wherein the sealing means includes means for filtering individual wave bands to identify specific elements, compounds or mixtures in the fluid medium.

44. The probe of claim 43, wherein the sealing means includes a bandpass filter disposed in a path of the electromagnetic wave for filtering an individual wave band to identify an element, a compound or a mixture in the fluid medium.

45. A probe for monitoring a fluid medium comprising:

a base having an upper and a lower surface, and a plurality of holes extending from the upper to the lower surface;

at least one fiber optic in a hole of the plurality of holes; and means for sealing the plurality of holes and for transmitting an electromagnetic wave;

further comprising an electromagnetic source and wherein a bandpass filter is disposed between the electromagnetic source and the sealing means.

46. A probe for monitoring a fluid medium comprising:

a base having an upper and a lower surface, and a plurality of holes extending from the upper to the lower surface;

at least one fiber optic in a hole of the plurality of holes; and means for sealing the plurality of holes and for transmitting an electromagnetic wave;

further comprising a temperature sensitive element adjacent the sealing means facing away from the fluid medium and toward the at least one fiber optic.

47. A biomedical probe, comprising:

a sleeve comprising a hypodermic needle;

a fiber optic bundle housed in the sleeve for emitting and collecting an electromagnetic wave and at least one fiber optic, in collecting an electromagnetic wave and at least one fiber optic, in the sleeve, having a longitudinal axis and a fluid-facing end surface shaped to increase its electromagnetic collection efficiency, wherein the longitudinal axis is not normal to the fluid-facing end surface; and further comprising a connector attached to a fiber optic of the fiber optic bundle and a sealing window adjacent the fiber optic to form a vacuum or gas sealed chamber.

48. A probe for monitoring a fluid medium, comprising:

a base having an upper surface and a lower surface, and having at least one hole extending from the upper to the lower surface;

at least one fiber optic in the hole; and a deflectable diaphragm, disposed across the hole, capable of transmitting an electromagnetic wave; and a sleeve housing the base and the diaphragm and providing strength and rigidity to the base.

49. The biomedical probe of 48, wherein the at least one fiber optic comprises a fiber optic pair for emitting and collecting an electromagnetic wave.

50. A probe for monitoring a fluid medium, comprising:

a first fiber optic having a first longitudinal axis and a first fluid-facing end surface shaped to increase its electromagnetic collection efficiency; and a second fiber optic having a second longitudinal axis and a second fluid-facing end surface, wherein the first and second fiber optic axes are substantially parallel to each other at the first and second fluid-facing ends, and wherein the first longitudinal axis is not normal to the first fluid-facing end surface;

wherein the first and second fiber optic have a cone-shaped fluid-facing end surface.

51. The probe of claim 50, wherein the cone-shaped end defines an angle of less than about 45 degrees with respect to a plane perpendicular to the fiber optic axes at the fluid-facing end surfaces.

52. The probe of claim 50, further comprising a sleeve housing the first and the second fiber optic.

53. A probe for monitoring a fluid medium, comprising:

a first fiber optic having a first longitudinal axis and a first fluid-facing end surface shaped to increase its electromagnetic collection efficiency; and a second fiber optic having a second longitudinal axis and a second fluid-facing end surface, wherein the first and second fiber optic axes are substantially parallel to each other at the first and second fluid-facing ends, and wherein the first longitudinal axis is not normal to the first fluid-facing end surface;

wherein each of the first and second fiber optics has a convex fluid-facing end surface.

54. A probe for monitoring a fluid medium, comprising:

a first fiber optic having a first longitudinal axis and a first fluid-facing end surface shaped to increase its electromagnetic collection efficiency; and a second fiber optic having a second longitudinal axis and a second fluid-facing end surface, wherein the first and second fiber optic axes are substantially parallel to each other at the first and second fluid-facing ends, and wherein the first longitudinal axis is not normal to the first fluid-facing end surface;

wherein the first and second fiber optic terminate in a single convex-shaped fluid-facing end surface.

55. A probe for monitoring a fluid, comprising:

a fiber optic bundle for emitting and collecting an electromagnetic wave from a fluid-facing end, wherein the bundle includes a plurality of axis which are substantially parallel to each other at the fluid-facing end and wherein at least one of the fiber optics of the bundle has a longitudinal axis and a fluid-facing end surface shaped to increase its electromagnetic collection efficiency, wherein the longitudinal axis is not normal to the fluid-facing end surface;

wherein the bundle has a truncated cone-shaped fluid-facing end surface.

56. The probe of claim 55, wherein the bundle includes a source fiber which is surrounded by a plurality of collecting fiber optics.

57. The probe of claim 56, wherein each end of the plurality of collecting fiber optics defines an angle of less than about 45 degrees with respect to a plane perpendicular to an axis of the source fiber optic.

58. A probe for monitoring a fluid, comprising:

a fiber optic bundle for emitting and collecting an electromagnetic wave from a fluid-facing end, wherein the bundle includes a plurality of axis which are substantially parallel to each other at the fluid-facing end and wherein at least one of the fiber optics of the bundle has a longitudinal axis and a fluid-facing end surface shaped to increase its electromagnetic collection efficiency, wherein the longitudinal axis is not normal to the fluid-facing end surface;

wherein the bundle includes collecting fiber which is surrounded by a plurality of source fiber optics.

59. A probe for monitoring a fluid, comprising:

a fiber optic bundle for emitting and collecting an electromagnetic wave from a fluid-facing end, wherein the bundle includes a plurality of axis which are substantially parallel to each other at the fluid-facing end and wherein at least one of the fiber optics of the bundle has a longitudinal axis and a fluid-facing end surface shaped to increase its electromagnetic collection efficiency, wherein the longitudinal axis is not normal to the fluid-facing end surface;

wherein the source fiber optic is surrounded by a plurality of collecting fiber optics; and wherein the collecting fiber optics terminate in a spherical shape.

60. A probe for monitoring a fluid, comprising:

a fiber optic bundle for emitting and collecting an electromagnetic wave from a fluid-facing end, wherein the bundle includes a plurality of axis which are substantially parallel to each other at the fluid-facing end and wherein at least one of the fiber optics of the bundle has a longitudinal axis and a fluid-facing end surface shaped to increase its electromagnetic collection efficiency, wherein the longitudinal axis is not normal to the fluid-facing end surface;

wherein the fiber optics includes a source fiber which is surrounded by a plurality of collecting fiber optics.

wherein the source fiber optic has a spherical shaped end and the collecting fiber optics define an angle of less than about 45 degrees with respect to a plane perpendicular to the fiber optic axis.

61. A probe for monitoring a fluid, comprising:

a fiber optic bundle for emitting and collecting an electromagnetic wave from a fluid-facing end, wherein the bundle includes a plurality of axis which are substantially parallel to each other at the fluid-facing end and wherein at least one of the fiber optics of the bundle has a longitudinal axis and a fluid-facing end surface shaped to increase its electromagnetic collection efficiently, wherein the longitudinal axis is not normal to the fluid-facing end surface;

wherein the fiber optic bundle has a cone-shape fluid-facing end surface.

62. The probe of claim 61, wherein the cone-shape fluid-facing end surface defines an angle of approximately less than about 45 degrees with respect to a plane perpendicular to the fiber optic axes at the fluid-facing end.

63. A probe for monitoring a fluid, comprising:

a fiber optic bundle for emitting and collecting an electromagnetic wave from a fluid-facing end, wherein the bundle includes a plurality of axis which are substantially parallel to each other at the fluid-facing end and wherein at least one of the fiber optics of the bundle has a longitudinal axis and a fluid-facing end surface shaped to increase its electromagnetic collection efficiency, wherein the longitudinal axis is not normal to the fluid-facing end surface;

wherein the fiber optic bundle comprises substantially square fiber optics.

64. A probe for monitoring a fluid medium, comprising:

a plurality of fiber optics each having a fluid-facing end for emitting and collecting an electromagnetic wave; and a diaphragm separating the fiber optics from the fluid medium, the diaphragm having a first major surface facing the fluid-facing ends of the fiber optics and a second major surface facing the fluid, wherein the second major surface is shaped in increase its electromagnetic collection efficiency;

wherein the second major surface of the diaphragm includes a truncated cone shape.

65. A probe for monitoring a fluid medium, comprising:

a plurality of fiber optics each having a fluid-facing end for emitting and collecting an electromagnetic wave; and a diaphragm separating the fiber optics from the fluid medium, the diaphragm having a first major surface facing the fluid-facing ends of the fiber optics and a second major surface facing the fluid, wherein the second major surface is shaped in increase its electromagnetic collection efficiency;

wherein the second major surface off the diaphragm includes a spherical shape.

66. A probe for monitoring a fluid medium, comprising:

a plurality of fiber optics each having a fluid-facing end for emitting and collecting an electromagnetic wave; and a diaphragm separating the fiber optics from the fluid medium, the diaphragm having a first major surface facing the fluid-facing ends of the fiber optics and a second major surface facing the fluid, wherein the second major surface is shaped in increase its electromagnetic collection efficiency;

wherein the second major surface of the diaphragm includes a partially spherical shape surrounded by a cone shaped annulus.

67. A probe for monitoring a fluid medium, comprising:

a plurality of fiber optics each having a fluid-facing end for emitting and collecting an electromagnetic wave; and a diaphragm separating the fiber optics from the fluid medium, the diaphragm having a first major surface facing the fluid-facing ends of the fiber optics and a second major surface facing the fluid wherein the second major surface is shaped in increase its electromagnetic collection efficiency;

wherein the second major surface of the diaphragm includes a cone shape.

68. A probe for monitoring a fluid medium, comprising:

a plurality of fiber optics each having a fluid-facing end for emitting and collecting an electromagnetic wave; and a diaphragm separating the fiber optics from the fluid medium, the diaphragm having a first major surface facing the fluid-facing ends of the fiber optics and a second major surface facing the fluid, wherein the second major surface is shaped in increase its electromagnetic collection efficiency;

wherein the second major surface of the diaphragm includes a concave periphery.

69. A probe for monitoring a fluid medium, comprising:

a plurality of fiber optics each having a fluid-facing end for emitting and collecting an electromagnetic wave; and a diaphragm separating the fiber optics from the fluid medium, the diaphragm having a first major surface facing the fluid-facing ends of the fiber optics and a second major surface facing the fluid, wherein the second major surface is shaped in increase its electromagnetic collection efficiency;

wherein the second major surface includes a shape selected from the group consisting of a truncated cone, a sphere, a partial sphere surrounded by a cone shaped annulus, a cone, and a concave cone periphery, or any combination of the shapes thereof.

70. A temperature probe for monitoring the temperature of a fluid medium, comprising:

a single crystalline diaphragm having a 100 plane and crystallographic axis of 110; and a first and a second temperature sensitive element in series with each other and disposed on a 100 plane, wherein the first element includes a first longitudinal axis oriented along the 110 crystallographic axis and the second element includes a second longitudinal axis oriented along a 90 degree angle with respect to the 110 crystallographic axis.

71. A probe for monitoring a fluid medium, comprising:

a first fiber optic having a fluid facing end;

a second fiber optic having a fluid facing end and a non-fluid facing end, wherein the fluid facing ends of the first and second fiber optics are substantially opposite one another and separated by the fluid being monitored so that an electromagnetic wave is transmitted through the fluid between the fluid facing ends;

a reflector, facing the non-fluid facing end of the second fiber optic, for reflecting the wave after being transmitted by the second fiber optic in a predetermined direction; and a third fiber optic having an end substantially opposite the predetermined direction.

72. The probe of claim 71, wherein the third fiber optic emits the wave toward the reflector which reflects the wave to the second fiber optic to be collected and then emitted into the fluid being monitored and then collected by the fluid facing end of the first fiber optic.

73. The probe of claim 71, wherein the first fiber optic comprises a fluid core.

74. The probe of claim 73, wherein the second fiber optic comprises a fluid core.

75. The probe of claim 74, wherein the third fiber optic comprises a fluid core.

76. The probe of claim 74, wherein the third fiber optic comprises a fluid core.

77. The probe of claim 73, wherein the third fiber optic comprises a fluid core.

78. The probe of claim 71, wherein the second fiber optic comprises a fluid core.

79. The probe of claim 71, wherein the third fiber optic comprises a fluid core.

80. A biomedical device, comprising:

a sleeve comprising a hypodermic needle;

at least one fiber optic disposed in the sleeve; and a fiber optic tube having first and second ends, disposed in the sleeve, and adapted to function as an electromagnetic wave guide;

further comprising a first window for sealing off the first end and a second window for sealing off the second end forming a fluid core.

81. The biomedical device of claim 80, wherein the at least one fiber optic comprises a fiber optic pair for emitting and collecting an electromagnetic wave.

82. The biomedical device of claim 80, wherein the fiber optic tube emits electromagnetic radiation capable of eradicating undesirable cells and at least one fiber optic is adapted to monitor eradication, growth rate or the status of undesirable cells during an irradiation treatment.

83. A biomedical device, comprising:

a sleeve comprising a hypodermic needle;

at least one fiber optic disposed in the sleeve; and a fiber optic tube having first and second ends, disposed in the sleeve, and adapted to function as an electromagnetic wave guide;

further comprising a connector attached to the at least one fiber optic and a sealing window to form a vacuum or gas sealed chamber.

84. A biomedical device, comprising:

a sleeve comprising a hypodermic needle;

at least one fiber optic disposed in the sleeve; and a fiber optic tube having first and second ends, disposed in the sleeve, and adapted to function as an electromagnetic wave guide;

further comprising a first window for sealing off the first end and a second window for sealing off the second end forming a vacuum core.

* * * * *